US005763245A

United States Patent [19]

Greenplate et al.

[11] Patent Number: 5,763,245
[45] Date of Patent: *Jun. 9, 1998

[54] METHOD OF CONTROLLING INSECTS

[75] Inventors: John T. Greenplate, Manchester; Jay C. Pershing, Webster Groves; John P. Purcell, Ballwin; David R. Corbin, Chesterfield, all of Mo.

[73] Assignee: Monsanto Company, St. Louis, Mo.

[ * ] Notice: The term of this patent shall not extend beyond the expiration date of Pat. Nos. 5,554,369, 5,558,862 and 5,518,908.

[21] Appl. No.: 712,057

[22] Filed: Sep. 10, 1996

Related U.S. Application Data

[63] Continuation-in-part of Ser. No. 475,694, Jun. 7, 1995, Pat. No. 5,558,862, which is a continuation-in-part of Ser. No. 393,785, Feb. 24, 1995, Pat. No. 5,554,369, which is a division of Ser. No. 83,948, Jun. 28, 1993, Pat. No. 5,518, 908, which is a continuation-in-part of Ser. No. 937,195, Sep. 4, 1992, abandoned, which is a continuation-in-part of Ser. No. 762,682, Sep. 23, 1991, abandoned.

[51] Int. Cl.[6] .......................... C12N 15/63; C12N 15/82; A01H 5/00; A01G 13/00

[52] U.S. Cl. ........................ 435/172.3; 435/25; 435/69.1; 435/71.1; 435/189; 435/320.1; 435/375; 47/58; 424/93.2; 424/93.461; 424/94.4; 536/23.2; 536/23.7; 536/23.71; 800/205; 800/250; 800/255; 800/DIG. 27; 800/DIG. 56

[58] Field of Search ............................... 800/DIG. 27, 56, 800/205, 250, 255; 435/69.1, 71.1, 172.3, 320.1, 189, 375, 25; 424/94.4, 93.2, 93.461; 536/23.71, 23.7, 23.2; 514/44; 935/67, 74, 64, 9, 14, 29, 30; 47/58

[56] References Cited

U.S. PATENT DOCUMENTS

| | | | |
|---|---|---|---|
| 5,518,908 | 5/1996 | Corbin et al. | 435/172.3 |
| 5,530,197 | 6/1996 | Peferoen | 800/205 |
| 5,554,369 | 9/1996 | Corbin et al. | 424/94.4 |
| 5,558,862 | 9/1996 | Corbin et al. | 424/94.4 |

FOREIGN PATENT DOCUMENTS

| | | | |
|---|---|---|---|
| 0 385 962 | 9/1990 | European Pat. Off. | C12N 15/82 |
| WO 90/05788 | 5/1990 | WIPO | C12Q 1/60 |

OTHER PUBLICATIONS

Bagdasarian M., Lurz R., Ruckert, B., Franklin F.C.H., Bagdasarian M.M., Frey, J. and Timmis K.N., "Specific-purpose plasmid cloning vectors II. Broad host range, high copy number, RSF1010-derived vectors, and a host-vector system for gene cloning in Pseudomonas, " *Gene,* 16:237–47, 1981.

Bevan M., et al., "A chimaeric antibiotic resistance gene as a selectable marker for plant cell transformation," *Nature,* 304:184–187, 1983.

Burnette W.N., "Western Blotting: Electrophoretic transfer of proteins from Sodium Dodecyl Sulfate–Polyacrylamide-gels to unmodified nitrocellulose and radiographic detection with antibody and radioiodinated protein A," *Anal. Biochem,* 112:195–203, 1981.

Cornelissen B.J.C. et al., "Molecular characterization of messenger RNAs for 'pathogenesis–related' proteins 1a, 1b and 1c, induced by TMV infection of tobacco," *EMBO Journal,* 5:37–40, 1986.

Finney D.J., "Probit Analysis," Cambridge University Press, London, 1964.

Gallo L.L., "Pancreatic sterol ester hydrolase," *Methods Enzymol.,* 71:664–674, 1981.

Herrera–Estrella L., et al., *Nature*, "Expression of chimaeric genes transferred into plant cells using a Ti–plasmid–derived vector," 303:209–213, 1983.

Ishizaki T., Hirayama N., Shinkawa H., Nimi O., Murooka Y, "Nucleotide Sequence of the Gene for Cholesterol Oxidase from a *Streptomyces sp,*" *Journal of Bacteriology,* 171:596–601, 1989.

Kay R., et al., "Duplication of CaMV 35S Promoter Sequences Creates a Strong Enhancer for Plant Genes," *Science,* 236:1299–1302, 1987.

Klee H.J., et al., "Vectors for Transformation of Higher Plants," *Bio/Technology,* 3:637–642, 1985.

Knauf V.C. and Nester E., "Wide host range cloning vectors:A cosmid bank of an Agrobacterium Ti plasmid," *Plasmid,* 8:45–54, 1982.

Laemmli U.K., "Cleavage of structural proteins during the assembly of the head of bacteriophage T4," *Nature,* 227:680–685, 1970.

Marrone P.G., Ferri F.D., Mosley T.R., Meinke L.J., "Improvements in laboratory rearing of the southern corn rootworm, *Diabrotica undecimpuncta howardi*Barber (Coleopter: Chrysomelidae) on an artificial diet and corn" *Journal of Economic Entomology,* 78:290–293, 1985.

Matsudaira P., "Sequence from picomole guantities of proteins electroblotted onto polyvinylidene difluoride membranes," *Journal of Biol. Chem.,* 262–10035–10038, 1987.

Moore S. and Stein W.H., "Chromatographic determination of amino acids by the use of automatic recording equipment," *Methods in Enzymology,* 6:819–831, 1963.1992.

(List continued on next page.)

*Primary Examiner*—Charles C. P. Rories
*Attorney, Agent, or Firm*—Arnold, White & Durkee

[57] ABSTRACT

3-Hydroxysteroid oxidase in combination with *Bacillus thuringiensis* CryIA(b) or CryIA(c) crystal proteins or polypeptides controls insects, particularly lepidopterans. The combination when applied to larvae of several lepidopterans indicated significant effects on mortality and stunting and indicated responses that were statistically significant over those expected from additive, independent action. Cholesterol oxidase and CryIA(b) crystal protein were also effective against black cutworm neonates when co-expressed in transgenic corn and tested in a detached leaf assay.

18 Claims, 3 Drawing Sheets

OTHER PUBLICATIONS

Purcell J., Greenplate J.T., and Sammons R.P., "Examination of midgut luminal proeinase activites in six economically important insects." *Insect Biochem. Molec. Biol.*, 22:41–47.

Schuler M.A., et al., "Closely related families of genes code for theα and α' subunits of the soybean 7S storage protein complex." *Nucleic Acids Research*, 10:8225–8244, 1982.

Smith A.G. and Brooks, C.J.W., "Cholesterol oxidases: Properties and Applications." Journal of Steroid Biochemistry, 7:705–713, 1971.

Smith P.K., Krohn R.I., Hermanson G.T., Mallia A.K., Gertner F., Provenzano M.D., Fujimoto E.K., Goeke M.N., Olson B.J., Klenk, D.C. "Measurement of protein using bicinchoninic acid." *Analytical Biochemistry*, 150:76–85, 1985.

Winter et al., "The inhibition of petunia hsp70 mRNA processing $CdCl_2$ stress." *Mol. Gen. Genet.*, 221(2):315–319, 1988.

Yanisch–Perron C., Viera J., and Messing J., "Improved M13 phage cloning vectors and host strains: nucleotide sequences of the M13mp18 and pUC19 vectors." *Gene*, 33:103–119, 1985.

METHOD OF CONTROLLING INSECTS

The application is a continuation-in-part of U.S. Ser. No. 08/475,694 filed Jun. 7, 1995, now U.S. Pat. No. 5,558,862 issued Sep. 24, 1996, which is a continuation-in-part of U.S. Ser. No. 08/393,785 filed Feb. 24, 1995, now U.S. Pat. No. 5,554,369 issued Sep. 10, 1996, which is a Division of U.S. Ser. No. 08/083,948 filed Jun. 28, 1993, now U.S. Pat. No. 5,518,908 issued May 21, 1996, which is a continuation-in-part of U.S. Ser. No. 08/937,195 filed Sep. 4, 1992, now abandoned, which is a continuation-in-part of U.S. Ser. No. 07/762,682 filed Sep. 23, 1991, now abandoned.

FIELD OF THE INVENTION

This invention relates to a method of controlling insects, including lepidopterans and boll weevils, by use of a cholesterol oxidase, alone or in combination with a crystal protein from Bacillus thuringiensis which may be applied directly to the plant or produced thereon by microorganisms or by genetically modifying the plant to produce the enzyme, and to genes, microorganisms, and plants useful in that method.

BACKGROUND OF THE INVENTION

The use of natural products, including proteins, is a well known method of controlling many insect pests. For example, endotoxins of Bacillus thuringiensis (B.t.) are used to control both lepidopteran and coleopteran insect pests. Genes producing these endotoxins have been introduced into and expressed by various plants, including cotton, tobacco, and tomato. There are, however, several economically important insect pests that are not susceptible to B.t. endotoxins. One such important pest is the cotton boll weevil. There is also a need for additional proteins which control insects for which B.t. provides control in order to manage any development of resistance in the population.

It is therefore an object of the present invention to provide proteins capable of controlling insects, such as boll weevil and lepidopterans, and genes useful in producing such proteins. It is a further object of the present invention to provide genetic constructs for and methods of inserting such genetic material into microorganisms and plant cells. It is another object of the present invention to provide transformed microorganisms and plants containing such genetic material.

SUMMARY OF THE INVENTION

It has been discovered that proteins that catalyze the oxidation of 3-hydroxysteroids, for example, cholesterol, will control lepidopteran insects and boll weevils. They are lethal to boll weevil larvae and will interrupt the reproductive cycle of adults. They cause mortality and stunting of larvae of lepidopteran insects. The enzymes may be applied directly to plants or introduced in other ways such as through the application of plant-colonizing microorganisms or by the plants themselves, which have been transformed to produce the enzymes. 3-Hydroxysteroid oxidases (E.C.1.1.3.6) are naturally produced by microorganisms such as Streptomyces sp., Pseudomonas sp., Mycobacterium sp., Schizophyllum commune, Nocardia sp., and Rhodococcus sp. [Smith et al., 1976, and Long et al., 1990.]. Preparations of enzymes from several different sources are available from Sigma Chemical Company, St. Louis, Missouri.

New Streptomyces genes that control the expression of 3-hydroxysteroid oxidase have been isolated and sequenced. These new genes or genes from other known producers of 3-hydroxysteroid oxidase may be inserted into a transformation vector cassette which is used to transform plant-colonizing microorganisms which when applied to plants express the genes producing a 3-hydroxysteroid oxidase, thereby providing control of lepidopterans and boll weevil. Alternatively, genes which function in plants and encode the subject enzymes may be inserted into transformation vector cassettes which may be incorporated into the genome of the plant, which then protects itself from attack by expressing the gene and producing a 3-hydroxy-steroid oxidase. Additionally, the plant may also be transformed to co-express B.t. genes which express proteins for the control of other insects. Examples of plants transformed to express B.t. genes are disclosed in European Patent Publication No. 0385 962, which corresponds to U.S. Ser. No. 476,661, filed Feb. 12, 1990 [Fischhoff et al.], which is incorporated herein by reference.

In accomplishing the foregoing, there is provided, in accordance with one aspect of the present invention, a method of controlling insect infestation of plants by applying to the plant environment or plant seed an insecticidally effective amount of protein toxin for ingestion by the insect, comprising providing a 3-hydroxysteroid oxidase for ingestion by the insect or by providing by admixture or in tandem an insecticidally effective amount of a 3-hydroxysteroid and a B.t crystal protein. Particularly preferred crystal proteins are CryIA(b) and CryIA(c).

In accordance with another aspect of the present invention, there is provided a recombinant, double-stranded DNA molecule comprising in operative sequence:

a) a promoter which functions in plant cells to cause the production of an RNA sequence; and b) a structural coding sequence that encodes 3-hydroxysteroid oxidase;

c) a 3' non-translated region which functions in plant cells to cause the addition of polyadenylate nucleotides to the 3' end of the RNA sequence, wherein said promoter is heterologous with respect to the structural coding sequence and wherein said promoter is operatively linked with said structural coding sequence, which is in turn operably linked with said non-translated region.

In accordance with another aspect of the present invention, there is provided a method of producing genetically transformed plants which express an effective amount of a 3-hydroxysteroid oxidase, comprising the steps of:

a) inserting into the genome of a plant cell a recombinant, double-stranded DNA molecule comprising (i) a promoter which functions in plant cells to cause the production of an RNA sequence;

(ii) a structural coding sequence that encodes for 3-hydroxysteroid oxidase; and (iii) a 3' non-translated region which functions in said plant cells to cause the addition of polyadenylate nucleotides to the 3' end of the RNA sequence, wherein said promoter is heterologous with respect to the structural coding sequence and wherein said promoter is operatively linked with said structural coding sequence, which is in turn operably linked with said non-translated region;

b) obtaining transformed plant cells; and c) regenerating from the transformed plant cells genetically transformed plants which express an insecticidally effective amount of sterol oxidase.

There is also provided, in accordance with another aspect of the present invention, bacterial and transformed plant cells that contain DNA comprised of the above-mentioned elements (i), (ii), and (iii).

Yet another aspect of the invention is the discovery of a synergistic effect of *Bacillus thuringiensis* CryIA(c) or CryIA(b) proteins with cholesterol oxidase against lepidopteran pests. More particularly, combinations of CryIA(c) or CryIA(b) and CO are disclosed that are more effective against lepidoptera larvae than the oxidase or either crystal protein administered alone.

As used herein, the term "controlling insect infestation" means reducing the number of insects which cause reduced yield, either through mortality, retardation of larval development (stunting), or reduced reproductive efficiency.

As used herein, the term "structural coding sequence" means a DNA sequence which encodes for a polypeptide, which may be made by a cell following transcription of the DNA to mRNA, followed by translation to the desired polypeptide.

As used herein, the term "plant-colonizing microorganism" means a microorganism capable of colonizing a "plant environment" and expressing the protein 3-hydroxysteroid oxidase in the plant environment such that the microorganisms can exist in a symbiotic or non-detrimental relationship with the plant. Examples of such plant-colonizing microorganisms are provided below.

As used herein, the term "plant environment" means the surface of the plant, e.g. leaf, stem, buds, stalk, floral parts, root surface, the "rhizosphere", i.e. the soil which surrounds and may be influenced by the roots of the plant., and/or extracellular areas within the plant itself, i.e. the plant vasculature.

BRIEF DESCRIPTION OF THE DRAWINGS

Figure 1:
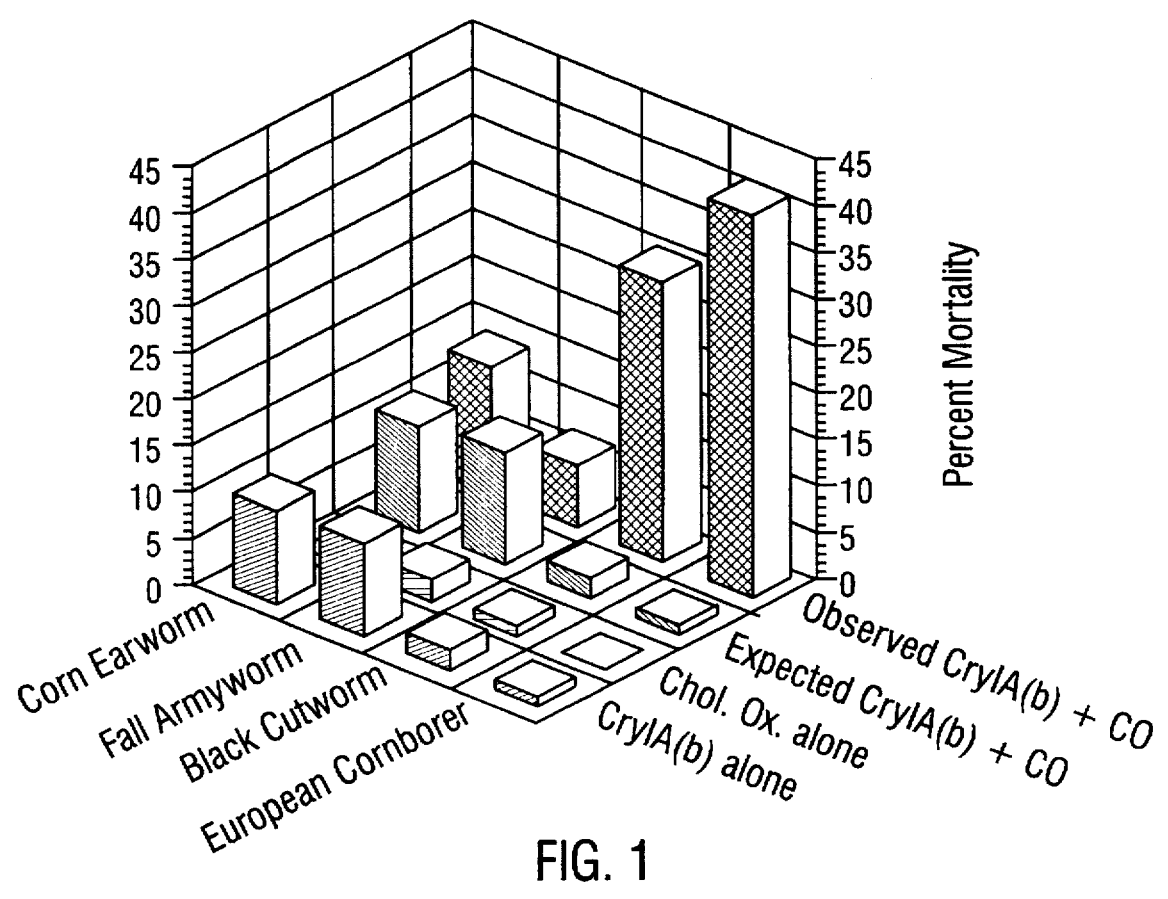

FIG. 1 shows effects of CryIA(b) and cholesterol oxidase (alone and in tandem) on neonate larvae of several lepidopteran corn pest. (CryIA(b) concentration=0.05 ppm for European cornborer, 10 ppm for corn earworm, 15 ppm for others; Cholesterol oxidase concentration=15 ppm for all insects.

FIG. 2 shows effects of CryIA(c) and cholesterol oxidase (alone and in tandem) on neonate larvae of several lepidopteran cotton pests. CyrIA(c) concentration=0.05 ppm for tobacco budworm, 15 ppm for bollworm and armyworm; Cholesterol oxidase concentration=15 ppm for all insects.

FIG. 3 shows effects of CryIA(b) and cholesterol oxidase alone and in tandem in the diet on 1st and 3rd instar larvae of the black cutworm Agrotis ipsilon CryIA(b) concentration=15 ppm; cholesterol oxidase concentration=15 ppm.

DETAILED DESCRIPTION OF THE INVENTION

3-Hydroxysteroid oxidases catalyze the oxidation of the 3-hydroxy group of 3-hydroxysteroids to produce ketosteroids and hydrogen peroxide. They are capable of catalyzing the oxidation of various 3-hydroxysteroids, such as, for example, cholesterol. Most of the previously known 3-hydroxysteroid oxidases are called "cholesterol oxidases" (enzymatically catalogued as E.C. #1.1.3.6) but cholesterol is only one of the 3-hydroxysteroid substrates, not the only one. The use of all 3-hydroxysteroid oxidases and the genes encoding such proteins, for the purpose of controlling insects, are within the scope of the present invention. 3-Hydroxysteroid oxidases are commercially available for use as reagents for serum cholesterol assays. For example, Sigma Chemical Company, St. Louis, Miss., offers three such 3-hydroxy-steroid oxidases (denominated as cholesterol oxidases), one from a *Streptomyces* sp., one from a *Pseudomonas fluorescens*, and one from a *Brevibacterium*. Two other sources of 3-hydroxysteroid oxidase, two streptomycetes denominated A19241 and A19249, each of which produce a 3-hydroxysteroid oxidase, have been isolated. The organisms were collected in Madagascar. When these organisms were cultured according to usual methods the culture filtrates were found to affect insect larvae as described below.

A seed culture of A19249 was started in 55 mL sterile Tryptone-Yeast Extract broth, pH 6.8, in a 250 mL shake flask. The seed was agitated at 250 rpm on a rotary shaker for 3 days at 30% C. A New Brunswick Bioflo II Bioreactor with a 2 L working volume was filled with "medium 202" ($MgSO_4 \cdot 7H_2O$ 2 g/L, $KH_2PO_4$ 0.5 g/L, NaCl 0.5 g/L, $CaCO_3$ 1 g/L, $ZnSO_4 \cdot H_2O$ (1 mg/mL stock) 5 mL/L, 100 mM FeEDTA 0.5 mL/L, Soluble Starch 5 g/L, Dextrose 2.5 g/L, Malt Extract 2.5 g/L, Soytone 5 g/L). The pH was adjusted to 6.5 with 2.5 N NaOH or 1 N HCl, and 1 mL/L of P2000, an antifoam agent was added. The bio-reactor was sealed and autoclaved for 25 min at 250% C. The seed, at 3 days growth, was used to inoculate the fermentor at 2% or 40 mL. The fermentation took place at 30% C with an airflow of 1 L/min and agitation running at 500 rpm. The fermentation was harvested after 40 h.

Each of these enzymes has demonstrated control of insects as shown below. The *P. fluorescens* 3-hydroxysteroid oxidase is immunologically distinct from the *Streptomyces* enzymes, but it also controls insects.

Other organisms producing 3-hydroxysteroid oxidases of the present invention may be identified by assaying culture filtrates or individual proteins for 3-hydroxysteroid oxidase activity using a spectrophotometric assay, described below, which measures hydrogen peroxide production in the presence of a 3-hydroxysteroid, for example, cholesterol [Gallo, 1981].

BIOEFFICACY ASSAYS

Boll Weevil Larvae Bioassay

Assays for activity against boll weevil larvae are carried out by incorporating the test sample into a agar liquid diet similar to that for southern corn rootworm [Marrone et al., 1985]. The test sample is substituted for the 20% water component. Neonate larvae are allowed to feed on the diet and mortality and growth stunting are evaluated.

The results of the assays of the 3-hydroxysteroid oxidases identified above are given in Table 1. Protein concentrations were determined spectrophotometrically with BCA protein reagent [Smith et al., 1985].

TABLE 1

| Protein Source | μg/mL | mUnits[1] per mL | BollWeevil % Mortality | Survivor Stunting |
|---|---|---|---|---|
| A19241 | 11 | 400 | 88 | |
| | 3.5 | 27 | 30 | Moderate |
| A19249 | 60 | 2100 | 60 | Severe |
| | 40 | 1400 | 70 | Severe |
| | 20 | 700 | 15 | Severe |
| | 15 | 525 | 5 | Moderate |
| | 10 | 350 | 10 | Moderate |
| | 5 | 175 | 10 | Slight |
| Sigma Strep | 57 | 1614 | 100 | |
| | 19 | 528 | 100 | |
| | 4.6 | 129 | 4 | Slight |
| Sigma *P. fluor.* | 44 | 692 | 100 | |
| | 19 | 290 | 39 | Slight |
| | 3.5 | 55 | 0 | |
| Sigma Brevibac. | 100 | 1480 | 40 | Moderate |
| | 60 | 888 | 40 | Slight |

[1]One Unit will oxidize 1 μmole of cholesterol/min when assayed with [cholesterol] = 129 μM.

Lepidopteran Larvae Bioassay

Lepidopteran larvae were tested on artificial diet treated with the indicated amount of the A19249 3-hydroxysteroid oxidase (cholesterol oxidase) for six days. The results are shown in Table 2.

An extended test was performed with tobacco budworm larvae to test the effect of the stunting noted in the six-day test. Tobacco budworm eggs were added to artificial diet (as described above) containing either buffer or 100 ppm A19249 3-hydroxysteroid oxidase (cholesterol oxidase). After seven days, some mortality as compared to the controls was noted. Surviving larvae were moved to fresh diet (control or treated, as appropriate). Percent mortality (corrected for control mortality) is reported for the 7 day and 10 day periods in Table 2A. The corrected number of larvae was 23.

TABLE 2

| Insect | Stage | Dose (µg/mL) | Stunting |
|---|---|---|---|
| tobacco budworm | egg/lv | 30 | 0 |
|  | lv | 100 | 86% |
| corn earworm | lv | 50 | 0 |
|  | lv | 100 | 35% |
| fall army worm | lv | 30 | 0 |
| tobacco hornworm | lv | 30 | 0 |
|  | lv | 100 | 30% |
| pink bollworm | lv | 50 | 0 |
|  | lv | 100 | 30% |
| European cornborer | lv | 50 | 0 |
|  | lv | 100 | 46% |
| beet armyworm | lv | 100 | 76% |
| black cutworm | lv | 100 | 68% |

TABLE 2A

| Interval (days) | Percent Mortality |
|---|---|
| 7 | 20 |
| 10 | 61 |
| 14 | 80 |

Boll Weevil Larval Age Difference Test The die incorporation study described above was performed to determine relative sensitivities of neonate and older (2nd instar) boll weevil larvae to the Sigma *Streptomyces* 3-hydroxysteroid oxidase (cholesterol oxidase). The mortality results shown in Table 3 reflect an eight-fold difference in susceptibility at six days exposure. This difference disappears after two weeks of exposure.

TABLE 3

| | $LC_{50}$ values (ppm in diet) | | |
|---|---|---|---|
| | 6 days | 12 days | 16 days |
| neonate | 8.3 | 5.3 | 4.8 |
| 2nd instar | 66.7 | 12.5 | 6.5 |

Boll Weevil Reproduction Test

3-Hydroxysteroid oxidases, in addition to lethal effects on larvae, will also affect the reproductive cycle of adult boll weevils, as demonstrated by the following study.

Preoviposition: Approximately 220 adult boll weevils, collected within 2 days of emergence, were divided into two groups. One was fed standard diet and the other was fed standard diet containing 48 ppm 3-hydroxysteroid oxidase from Sigma (*Streptomyces*). The adults were allowed to feed and mate for four days at which time mortality was determined. The results are reported in Table 4.

Oviposition study: These two groups of adults were then divided into two subgroups and individually placed on artificial, enzyme-containing or control bolls. Artificial bolls were constructed of standard diet, with or without 48 ppm 3-hydroxysteroid oxidase, and encased in paraffin containing 1% cottonseed oil. After three days at 27% C, the adults were removed and ten bolls from each of the four groups were removed and examined for eggs. The remaining bolls were incubated for an additional 7 days at 27% C to allow development of larvae. The bolls were then dissected and the eggs and larvae, dead and surviving, were counted. The results are reported in Tables 5 and 6.

Group 1=Control Adults placed on control bolls
Group 2=Control Adults placed on treated bolls
Group 3=Enzyme-fed adults placed on control bolls
Group 4=Enzyme-fed adults placed on treated bolls

TABLE 4

| | Initial # | Survivors |
|---|---|---|
| Adults fed control diet | 111 | 110 |
| Adults fed treated diet | 110 | 107 |

TABLE 5

| | Bolls with eggs or larvae | No. of females |
|---|---|---|
| Group 1 | 20 | 29 |
| Group 2 | 17 | 26 |
| Group 3 | 9 | 27 |
| Group 4 | 2 | 17 |

TABLE 6

| | Total number larvae | Number live larvae |
|---|---|---|
| Group 1 | 24 | 24 |
| Group 2 | 18 | 1 |
| Group 3 | 3 | 1 |
| Group 4 | 0 | — |

The above results confirm the effects of 3-hydroxysteroid oxidase on boll weevil larvae when apparently normal larvae are challenged with the enzyme in their diet. Data in Table 5 indicate that adults fed 3-hydroxysteroid oxidase do not oviposit normally, even when presented with control bolls. It is also apparent that normal adults will readily oviposit in bolls containing the enzyme (Table 5). Table 6 data suggest a reduction of egg viability when adults are fed 3-hydroxysteroid oxidase during the pre-oviposition period. Although no direct mortality in adults was observed (Table 4) during the observation period, there is evidence of profound 3-hydroxysteroid oxidase effects on the adults' ability to develop and/or oviposit viable eggs.

MODE OF ACTION STUDIES

The following studies show that 3-hydroxysteroid oxidase has a direct effect on the insect itself and that the activity demonstrated in the studies described above cannot be attributed to the enzymes effect on the insect's diet, for example by sterol depletion. Lepidopteran larvae and boll weevils are most susceptible to the enzyme. It is believed that this specificity is due to the effect of 3-hydroxysteroid oxidase on the midgut of the insect as explained in more detail below. It has been observed that the boll weevil midgut has a proteinase composition which is more like lepidopterans than that of coleopteran (Purcell, et al., 1992), which probably explains why boll weevils and lepidopterans are the most sensitive to the enzyme. Other insects with similar midgut physiologies may also be controlled by 3-hydroxysteroid oxidase. In addition, 3-hydroxysteroid oxidases other than those tested and reported herein may control a different spectrum of insects with different midgut physiologies.

Cotton Seed Diet Assay

The Southern corn rootworm diet used in the assay described above was the control. Two treatment diets were made by mixing 30 g of one of two types of cottonseed flour into 170 mL of a 1.6% agar solution at 50% C, containing 0.13% propionic acid, 0.014% phosphoric acid, and 30 mg each of streptomycin sulfate and chlortetracycline. Before mixing, 10% KOH was used to adjust the pH to 6.2. One test diet utilized raw cottonseed flour (Sigma) as the nutrient source; the other utilized Pharmamedia™ (Traders Protein), a flour made up of cottonseed embryos. The diets were incubated in a water bath at 40% C. Dilutions of the Sigma Streptomyces 3-hydroxysteroid oxidase (cholesterol oxidase) were incorporated into the diets as described above. Boll weevil larvae were allowed to feed and mortality rates were determined after six days. The results shown in Table 7 demonstrate that the enzyme is lethal to boll weevil larvae in the presence of cotton plant components.

TABLE 7

| Enzyme conc. | Diet (% Corrected Boll Weevil Mortality) | | |
|---|---|---|---|
| (ppm) | Control | Cottonseed | Cotton embryo |
| 10 | 0* | 27* | 14* |
| 20 | 29** | 85** | 58** |
| 60 | 100 | 100 | 82*** |

*= Slight survivor stunting
**= Moderate survivor stunting
***= Severe survivor stunting In addition, tobacco budworm larvae are 68% stunted when exposed to 3-hydroxysteroid oxidase (100 ppm) in cottonseed diet (made with Pharmamedia™ flour).

Homogenized cotton leaf tissue assay

In order to test 3-hydroxysteroid oxidase against boll weevil larvae in a host tissue diet environment, a study was conducted in which cotton leaf tissue was the only nutritional component of an agar-based diet. Two cotton leaves (each approx. 5 inches wide ) with stems were homogenized at 50% C into 170 mL of a 1.6% agar solution containing 0.13% propionic acid, 0.014% phosphoric acid, and 30 mg each of streptomycin sulfate and chlortetracycline. Before addition of the leaves, 10% KOH was used to adjust the pH of the agar solution to 6.2. The leaf "diet" was allowed to cool to 40% C. Dilutions of cholesterol oxidase and a water control were incorporated into the leaf "diet", poured into insect diet trays and allowed to cool. Boll weevil eggs were added to the diet wells. The assay was evaluated six days later. The results shown in Table 8 demonstrate that the enzyme maintains its insecticidal activity in the presence of cotton leaf tissue. This illustrates that the enzyme is insecticidal in the presence of intact cotton tissue and cells. Since the sterols in these leaf homogenates would presumably not all be accessible to the exogenously added 3-hydroxysteroid oxidase, this suggests that the enzyme is not depleting the diet of all the necessary sterols and that the mode of action of 3-hydroxysteroid oxidase is not dependent on sterol depletion of the nutrient source. These results demonstrate that successful control of boll weevil should be attained when the 3-hydroxysteroid oxidase gene is expressed in cotton tissue.

TABLE 8

| | Bollweevils | |
|---|---|---|
| cholesterol oxidase | Initial | Survivors |
| 10 ppm | 24 | 20 |
| 50 ppm | 24 | 12 |
| 100 ppm | 24 | 0 |

Activity of Cholesterol Oxidase on Cotton Callus Tissue.

Two studies were performed using cotton callus as the assay feeding substrate. In both cases the arena was a 96-well insect diet tray; each well contained 0.5 mL of gelled 2% agar, with 0.13% propionic acid and 0.014% phosphoric acid, covered with a ½ inch filter paper disc. For each replicate, fifty to one hundred milligrams of cotton callus (Coker 312) was soaked in either water (control) or a 400 ppm cholesterol oxidase solution and placed in a diet tray well. A second instar boll weevil larva was added to each well, and the tray was covered with a sheet of mylar and sealed with a tacking iron. Assay duration was six days. The results shown in Table 9 demonstrate that the enzyme is active in cotton callus bioassays. This illustrates that the enzyme is insecticidal in the presence of intact cotton tissue and the bioactivity is seen when the enzyme is ingested with whole cotton cells and tissue. Since the sterols in this callus would presumably not all be accessible to the exogenously added 3-hydroxysteroid oxidase, this further demonstrates that the mode of action of 3-hydroxysteroid oxidase is not dependent on sterol depletion of the nutrient source. These results demonstrate that successful control of boll weevil should be attained when the 3-hydroxysteroid oxidase gene is expressed in cotton tissue.

TABLE 9

| | Percent corrected boll weevil mortality (N) | |
|---|---|---|
| | 1st study | 2nd study |
| Enzyme soaked callus | 36(12) | 54(24) |

Comparison of boll weevil $LC_{50}$ values for various diet assays

The table below summarizes the activity of 3-hydroxysteroid oxidase on boll weevil neonate larvae when presented in various diets. If the activity depended upon depletion of sterols from the diet then one would expect that the amount of enzyme required for boll weevil mortality would depend greatly upon the diet that is utilized in the assay since the amount and accessibility of the constituent sterols would vary widely in these assay mediums. The data shown in Table 10 demonstrate that $LC_{50}$ values obtained are very consistent from one type of assay to the next. This further demonstrates that the mode of action of 3-hydroxysteroid oxidase is not dependent on sterol depletion of the nutrient source but that the enzyme is directly active upon the boll weevil. These results demonstrate that successful control of boll weevil should be attained when the 3-hydroxysteroid oxidase gene is expressed in cotton tissue.

TABLE 10

| Diets | LC50 (ppm) | 95% confidence limits |
|---|---|---|
| artificial diet | 20.9 | 16.2–29.5 |
| cottonseed embryo | 13.6 | 3.6–22.2 |
| cottonseed flour | 11.8 | 6.3–15.5 |
| cotton leaf | 18.4 | 14.8–23.5 |

Spectrum of insecticidal activity of 3-hydroxysteroid oxidase

Three other coleopteran species, three other insects, and one mite species were evaluated for susceptibility to Sigma *Streptomyces* 3-hydroxysteroid oxidase (Table 11). Bioassays were evaluated after 4 to 7 days to measure acute effects of the enzyme on the insects' growth and survival. No significant acute effects (mortality or stunting of larval growth) were observed in these short term assays. The long term effects of exposure to cholesterol oxidase were not determined for these insects. The bioactivity against tobacco budworm demonstrates that longer exposure to the enzyme resulted in greater mortality (Table 2a, above). Thus deleterious effects on larval growth and development of the insects listed in Table 11 and other insects may result from chronic ingestion of 3-hydroxysteroid oxidase. ("1 v"=larvae)

TABLE 11

| Insect | Stage | Dose (μg/mL) | Mortality (stunting) |
|---|---|---|---|
| corn rootworm | egg/lv | 30 | 0 |
|  |  | 100 | 0 |
| Colorado potato beetle | lv100 | 13 |  |
| German cockroach | nymph | 75 | 0 |
| yellow fever mosquito | lv | 15 | 0 |
| green peach aphid | all stgs | 30 | 0 |
|  |  | 100 | 0 |
| two spot spider mite | adult | 150 | 0 |
| sugarcane rootsalk borer | lv | 100 | 0 |

Mode of Action Theory

While not being bound by this theory, it is believed that the 3-hydroxysteroid oxidase enzyme kills or stunts boll weevil larvae and stunts the growth of lepidopteran larvae by some action in the gut after ingestion. There are no lethal or stunting effects from feeding boll weevil or lepidopteran larvae a diet sample that was incubated for one week with a 3-hydroxysteroid oxidase and then boiled prior to using it in the above assay.

This further demonstrates that the mode of action of 3-hydroxysteroid oxidase is not dependent on sterol depletion of the nutrient source but that the enzyme is directly active upon the insect.

Nor do cholestenone or hydrogen peroxide, the products of enzymatic action on cholesterol, exhibit any lethal effects against boll weevil when incorporated at up to 200 &M in the standard diet described above. The addition of catalase (E.C. #1.11.1.6) to 3-hydroxy-steroid oxidase in the bioassay does not block the lethal effects of 3-hydroxysteroid oxidase on boll weevil, providing further evidence that in vitro generation of hydrogen peroxide is not the mode of action.

The enzymatic action in the gut is believed to be oxidation of the 3-hydroxysteroid(s) of the cell membranes in the lining of the gut. The effects of ingested 3-hydroxysteroid oxidase on the midguts of boll weevil larvae have been studied. The midguts of boll weevil larvae (neonate and second instar at initiation of assay) feeding on diets containing sublethal doses of 3-hydroxysteroid oxidase were dissected out. Representative midguts were immediately placed in fixative and analyzed microscopically for morphological changes. Disruption of the epithelial cell layer was observed in the guts of larvae ingesting low doses, and complete lysis of the cells was observed from the higher doses. There was a good correlation of the morphological changes with the observed mortality over the 3-hydroxysteroid oxidase concentration range in the diet. Parallel midguts were dissected and homogenized and found to contain active 3-hydroxysteroid oxidase in enzymatic assays. This study demonstrates that the mode of action of 3-hydroxy-steroid oxidase on insect larvae involves lysis of the epithelial cell layer, possibly by oxidation of its membrane cholesterol or other 3-hydroxysteroid.

ENZYME IDENTIFICATION

The active proteins from the Madagascar *Streptomyces* microorganisms were isolated, purified, partially sequenced, and identified as 3-hydroxysteroid oxidases.

Protein Isolation

Each culture filtrate was purified by first sizing on YM 10 membranes (Amicon) to a [>10 kDa] fraction, followed by multiple chromatography runs on an FPLC Mono Q HR10/10 (Pharmacia LKB, Piscataway, NJ) column. For chromatography on the Mono Q column, the samples were loaded on the column in 25 mM Hepes pH 7.5 and eluted with a gradient to 1.0 M KCl in 25 mM Hepes pH 7.5. Fractions were collected and aliquots of each were filtered through 0.2 & Acrodisc syringe tip filters. Each was tested in the boll weevil assay described above. Aliquots of insecticidally active fractions were electrophoresed on SDS-PAGE [Laemmli, 1970] using a Daiichi Double Gel Device and 10–20% mini-gel. Proteins were visualized by silver staining using Daiichi silver stain reagent kit. The active enzymes of the present invention, isolated from the novel microorganisms, were found to be a 52.5 kDa protein.

Amino Acid Sequences

An SDS-PAGE gel of the protein produced by *Streptomyces* A19241, isolated as above, was blotted onto PVDF paper (Immobilon, Millipore Corp.) using the protocol of Matsudaira [Matsudaira, 1987]. The N-terminus was sequenced using automated Edman degradation chemistry. A gas phase sequencer (Applied Biosystems, Inc.) was used for the degradation using the standard sequencer cycle. The respective PTH-aa derivatives were identified by reverse phase HPLC analysis in an on-line fashion employing a PTH analyzer (Applied Biosystems, Inc.) fitted with a Brownlee 2.1 mm i.d. PTH-C18 column. For internal sequences, digestions were carried out on purified 3-hydroxysteroid oxidase from A19249 using trypsin (TPCK-treated, from Worthington Biochemicals Corp., Freehold, NJ). Fragments were then purified by reverse phase HPLC and sequenced in an N-terminal fashion.

The resulting partial sequences were compared to known proteins and a strong (71%) homology was found with the reported fourteen amino acid sequence at the N-terminus of a 3-hydroxysteroid oxidase isolated from a Streptomyces species [Ishizaki et al., 1989]. The reported enzyme has an Mr of 54.9 kDa which agrees well with the $M_r$ of 52.5 kDa of the isolated enzyme.

Six internal fragments of the purified enzyme from A19249, also having homology to six regions of the reported enzyme, were sequenced. The fragments had 95, 76, 64, 58, 89, and 100 percent sequence identities.

Amino Acid Composition Determination and Comparison

The amino acid composition of the 3-hydroxysteroid oxidase produced by A19249 was determined and compared with the composition of the reported *Streptomyces* enzyme.

The samples were subjected to acid hydrolysis (6 N HCl, vapor phase hydrolysis using a Water's Picotag workstation, 24 hr. 110% C.). All analyses were performed after post-column derivation of the hydrolysates using ninhydrin [Moore et al., 1963]. A Beckman Model 6300 Auto analyzer was employed for the actual determinations. The S delta n/N statistic is used to compare two compositions in order to make a prediction about their relatedness. The formula for the statistic is:

$$\tfrac{1}{2}(n_{Ai}-n_{Bi})^2/N$$

where A is one composition, B is the other composition, i is each amino acid, n is the number of each amino acid, N is the total number of amino acids in the protein. If S delta n/N is <0.42, then there is a greater than 95% chance that the proteins are related. The smaller the value, the more closely the determined compositions match.

The S delta n/N statistic for the Al 9249 protein compared to the reported enzyme is 0.36, indicating that the two are highly related.

3-Hydroxysteroid Oxidase Assay

The identity of the enzyme was confirmed by testing its ability to oxidize a 3-hydroxysteroid, specifically cholesterol. The enzyme is added to a reagent mixture comprising horseradish peroxidase (20 U/mL), phenol (14 mM), 4-amino antipyrine (0.82 mM), Triton® X-100 (0.05%) and phosphate buffer (100 mM, pH 7). The sterol in isopropanol is then added and the absorbance at 500 nm monitored. One unit of activity is defined as the amount of enzyme required to oxidize 1 &mole of sterol per minute at 20% C.

The activity levels of the enzymes are reported in Table 12 for 3-hydroxysteroids representative of various classes of 3-hydroxysteroids. The enzyme sources are as follows:

1=A19249
2=A19241
3=Sigma Streptomyces
4=Sigma Pseudomonas

TABLE 12

| Sterol | Relative Rate for Enzymes | | | |
|---|---|---|---|---|
| | 1 | 2 | 3 | 4 |
| cholesterol | 100 | 100 | 100 | 100 |
| dihydrocholesterol | 56 | 56 | 59 | 69 |
| dehydrocholesterol | 13 | 12 | 7 | 47 |
| lathosterol | 28 | 34 | 27 | 71 |
| stigmasterol | 22 | 28 | 11 | 21 |
| sitosterol | 88 | 65 | 49 | 50 |
| campesterol* | 65 | 64 | 45 | 49 |
| fucosterol | 22 | 20 | 12 | 68 |
| lanosterol | <1 | <1 | <1 | 1 |
| ecdysone | <1 | <1 | <1 | <1 |
| 20-OH ecdysone | <1 | <1 | <1 | <1 |

Immunological Comparison of Enzymes

The Sigma Streptomyces enzyme is immunologically related to the 3-hydroxysteroid oxidases produced by the isolates of the present invention, numbers A19241 and 19249, as demonstrated by Western blotting [Burnette et al., 1981] using polyclonal antisera generated against the Sigma Streptomyces enzyme. The antisera recognized both enzymes produced by the isolates. The 3-hydroxysteroid oxidase from P. fluorescens was not recognized by the antisera. This demonstrates that immunologically distinct 3-hydroxysteroid oxidases are lethal to boll weevils.

GENETIC IDENTIFICATION

The 3-hydroxysteroid oxidase gene was isolated from one of the Streptomyces microorganisms isolated in Madagascar and its sequence determined.

Cloning of the 3-Hydroxysteroid Oxidase Gene from A19249

As discussed above, peptide sequences of purified 3-hydroxy-steroid oxidase from A19249 were obtained for four regions of the protein. These peptide sequences were compared to a database of known protein sequences, and this comparison revealed that the A19249 protein showed a high degree of homology to a known 3-hydroxy-steroid oxidase from Streptomyces [Ishizaki]. Comparing the A19249 peptide sequences to this known protein sequence, these peptides were assigned to their likely positions in the A19249 protein sequence. The sequence derived from the intact 3-hydroxysteroid oxidase from Al 9249 corresponded to a region near the N-terminus of the secreted form of the enzyme from the published sequence. From this it was concluded that the Al 9249 N-terminal peptide sequence was also likely to correspond to a "mature" secreted form of the protein lacking its putative secretory signal sequence. This was later confirmed by the DNA sequence analysis of the Al 9249 gene (see below). Three peptides were used to construct hybridization probes for isolation of the A19249 3-hydroxysteroid oxidase gene. Peptide N2 (SEQ ID NO:1) corresponded to N-terminal amino acids 29–43 of the known mature protein sequence (sequence without the putative signal peptide); peptide C1 (SEQ ID NO:2) to amino acids 434–449 of the mature protein sequence; and peptide C2 (SEQ ID NO:3) to amino acids 464–475 of the mature protein sequence.

N2 (SEQ ID NO:1): ValSerThrLeuMetLeuGluMetGlyGlnLeuTrpAsnGlnPro

C1 (SEQ ID NO:2): AlaPheAlaAspAspPheCysTyrHisProLeuGlyGlyCysValLeu

C2 (SEQ ID NO:3): AsnLeuTyrValThrAspGlySerLeuIleProGly

Based on these peptide sequences, three long nondegenerate oligonucleotides, corresponding to 3-hydroxysteroid oxidase peptide sequences from A19249 were designed using *Streptomyces* preferred codons. The oligonucleotides N2 (SEQ ID NO:4), C1 (SEQ ID NO:5), and C2 (SEQ ID NO:6) correspond to the peptides N2, C1, and C2 described above.

N2 Probe (SEQ ID NO:4): gtgtccaccctgatgctggagatgggccagctgtggaaccagccc

C1 Probe (SEQ ID NO:5): gccttcgccgacgacttctgctaccacccgctcggcggctgcgtcctg

C2 Probe (SEQ ID NO:6): aacctctacgtgaccgacggttcgctgatcccgggt

Probes N2 (SEQ ID NO:4), C1 (SEQ ID NO:5), and C2 (SEQ ID NO:6) were all used as hybridization probes on Southern blots of A19249 genomic DNA. All three probes hybridized to the same 2.2 kb band in BamHI digested DNA, but N2 (SEQ ID NO:4) hybridized to a different fragment than C1 (SEQ ID NO:5) and C2 (SEQ ID NO:6) did in SalI and BglII digests. This indicated that SalI and BglII cut within the coding sequence of the 3-hydroxysteroid oxidase gene from A19249, which was confirmed by DNA sequence analysis.

The 3-hydroxysteroid oxidase gene from A19249 was isolated using the three synthetic oligonucleotides as hybridization probes on a library of DNA fragments of A19249 DNA in a lambda phage vector. A library was made in lambda EMBL3 using partial-digest MboI DNA fragments of A19249. These probes were used to screen approximately 72,000 lambda phage plaques from the primary library. Primary plaque screening was performed using N2 (SEQ ID NO:4) plus C2 (SEQ ID NO:6). A total of recombinant plaques that hybridized to the N and C-terminal probes were picked and purified by a second round of hybridization screening with probes N2 (SEQ ID NO:4) and C2 (SEQ ID NO:6). Southern blot analysis revealed that, in five of six lambda clones analyzed, a 2.2 kb BamHI fragment hybridized to both the N and C-terminal probes. This result confirmed the earlier Southern hybridization analysis that indicated a 2.2 kb BamHI fragment contained the 3-hydroxysteroid oxidase gene. This 2.2 kb DNA fragment was cloned into plasmid vector pUC18 [Yanisch-Perron et al., 1985] in both orientations for further analysis. Restriction mapping showed that there were internal SalI and BglII sites as predicted by the Southern hybridization analysis. These sites are also conserved compared to the published 3-hydroxysteroid oxidase gene sequence. The BamHI fragment was further subcloned into four fragments for direct DNA sequencing.

Sequence Analysis of the 3-Hydroxysteroid Oxidase Gene

A total of 1865 nucleotides of DNA sequence from the 2.2 kb BamHI fragment were determined by direct DNA sequence analysis of subclones of this fragment using the dideoxy chain termination method. This sequence is identified as SEQ ID NO:7. This DNA sequence contains non-coding flanking regions at both the 3' and 5' ends. Analysis of this DNA sequence revealed a single long open reading frame that encodes a secretory signal peptide and the mature 3-hydroxysteroid oxidase protein of 43 and 504 amino acids, respectively. It is 84.37% identical to the published 3-hydroxysteroid oxidase nucleotide sequence. The derived amino acid sequence is 81.685% identical to the published 3-hydroxysteroid oxidase sequence. It is identified as SEQ ID NO: 8. Examination of the A19249 DNA sequence and comparison to the N-terminal amino acid sequence of intact 3-hydroxysteroid oxidase from A19249 revealed that the A19249 gene encoded a protein that includes a signal peptide sequence, which is apparently cleaved during secretion of the protein from the cells. Thus the N-terminus of the mature protein from Al 9249 begins with Ser—Gly—Gly—Thr—Phe, identified as SEQ ID NO:12.

GENETIC TRANSFORMATION

A 3-hydroxysteroid oxidase gene can be isolated from novel organisms or may be obtained from known sources, such as the *Rhodococcus* sp. described by Long et al., in WO 9005,788. This gene may then be used to transform bacterial cells or plant cells to enable the production of 3-hydroxysteroid oxidase and carry out methods of this invention. Examples of how this may be done with the gene of Al 9249 are given below.

Mutagenesis of the A19249 Gene

In order to incorporate the Al 9249 gene into vectors appropriate for expression of the 3-hydroxysteroid oxidase in heterologous bacterial or plant hosts, it was necessary to introduce appropriate restriction sites near the ends of the gene. The goals of this mutagenesis were to create cassettes that included the protein coding sequence with minimal noncoding flanking sequences and to incorporate useful restriction sites to mobilize these cassettes. Cassettes were designed that would allow mobilization of the intact coding sequence including the signal peptide or just the mature coding sequence. To incorporate these cassettes into appropriate bacterial or plant expression vectors, an NcoI restriction site was engineered at the N-terminus of the intact protein sequence or at the N-terminus of the mature protein sequence. A BamHI site was engineered just after the termination codon of the intact coding sequence. Three mutagenesis primers were designed to create these cassettes, as shown below. Mutagenesis with primer Chossn (SEQ ID NO:9) substituted three amino acids (MAT) for valine and asparagine at the N-terminus of the signal peptide of the intact protein and Chomnr (SEQ ID NO:10) added two amino acids (MA) at the N-terminus of the mature protein. This was necessary to allow incorporation of the NcoI restriction site. Mutagenesis with primer Cho3br (SEQ ID NO: 11) incorporated a BamHI site at the 3' end of the coding sequence. Primers Chomnr and Cho3br were used to direct formation of the antisense strand of DNA.

Chossn (SEQ ID NO:9): CTCAGGAGCA CGACCGCA-CAC (NcoI site underlined)

Chomnr (SEQ ID NO:10): GTGCCGCCGGAGG T GGGCGGTGGC (NcoI site underlined)

Cho3br (SEQ ID NO:11): GCCCOGCCCGTC T GTCAGGAACCCG (BamHI site underlined)

The resulting modified sequences were identified as SEQ ID NO:13 encoding for the intact protein and SEQ ID NO: 14 for the mature protein.

Expression of 3-Hydroxysteroid Oxidase in *E. coli*

The NcoI-BamHI fragments containing either the intact protein coding sequence or the mature protein coding sequence were inserted into a vector designed for protein expression in *E. coli*, vector pKK233-2 (Pharmacia LKB, Piscataway, NJ). pKK233-2 contains the IPTG-inducible trc promoter. The vector containing the intact (full length) protein coding sequence as modified (SEQ ID NO:13) is designated pMON20909. The vector containing the mature protein coding sequence as modified (SEQ ID NO:14) is designated pMON20907. *E. coli* XL1 Blue cells (Statagene, San Diego, CA) modified with pMON20909 expressed 3-hydroxysteroid oxidase at higher levels of enzymatic activity than cells modified with pMON20907. The protein was extracted and purified from 4 liters of IPTG-induced *E. coil* containing pMON 20909. The soluble fraction from sonicated bacterial lysate was concentrated and dialyzed, and then partially purified by Mono Q chromatography to yield 11 units of 3-hydroxysteroid oxidase activity. Western blot analysis indicates that the signal sequence of the intact protein is cleaved in *E. coli*, but the exact site of cleavage was not determined. Analysis of the recovered protein showed a five-fold reduction in enzymatic activity relative to the Al 9249 protein, but the loss has not been explained by DNA sequencing which found no alterations that would explain loss of enzymatic activity in plant protoplasts or *E. coli*.

The recovered protein was used in artificial diet overlay assays to determine the effects on boll weevil viability. The dose response curve for activity against boll weevil, based upon enzymatic activity units, was very similar to that originally observed with the Streptomyces and Al 9249 enzymes. The results are shown in Table 13. In addition, the recovered protein was tested against tobacco budworm and resulted in 88% stunting at a dose of 100 &g/ml.

TABLE 13

| | Dose | | |
|---|---|---|---|
| Sample | ppm | mU/ml | % Mortality |
| 1 | 250 | 1775 | 86*** |
| 2 | 75 | 533 | 64*** |
| 3 | 25 | 178 | 21** |
| 4 | 0 | 0 | 0 |

*= Slight survivor stunting
**= Moderate survivor stunting
***= Severe survivor stunting Expression of 3-Hydroxysteroid Oxidase in Plant Colonizing Bacteria To control boll weevil, it may be desirable to express 3-hydroxy-steroid oxidase in plant colonizing bacteria, and then apply this bacteria to the plant. As the boll weevil feeds on the plant, it ingests a toxic dose of 3-hydroxysteroid oxidase produced by the plant colonizers. Plant colonizers can be either those that inhabit the plant surface, such as *Pseudomonas* or *Agrobacterium* species, or endophytes that inhabit the plant vasculature such as Clavibacter species. For surface colonizers, the 3-hydroxysteroid oxidase gene may be inserted into a broad host range vector capable of replicating in these Gram-negative hosts. Examples of these such vectors are pKT231 of the IncQ incompatibility group [Bagdasarian et al., 1981] or pVK100 of the IncP group [Knauf, 1982]. For endophytes the 3-hydroxysteroid oxidase gene can be inserted into the chromosome by homologous recombination or by incorporation of the gene onto an appropriate transposon capable of chromosomal insertion in these endophytic bacteria.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bis-phos-phate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., PCT publication WO 84/02913).

The particular promoter selected should be capable of causing sufficient expression of the enzyme coding sequence to result in the production of an effective amount of 3-hydroxysteroid oxidase. A preferred promoter is a constitutive promoter such as FMV35S. It has been observed to provide more uniform expression of heterologous genes in the flowering portions of plants. Use of such a promoter with the 3-hydroxysteroid oxidase gene may provide greater protection of cotton bolls and squares from boll weevil damage, than other promoters.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987).

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs wherein the non-translated region is derived from the 5' non-translated sequence that accompanies the promoter sequence. As shown below, a plant gene leader sequence which is useful in the present invention is the petunia heat shock protein 70 (Hsp70) leader. [Winter et al.]

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of *Agrobacterium* tumor-inducing (Ti) plasmid genes, such as the nopaline synthase (NOS) gene and (2) plant genes like the soybean 7s storage protein genes and the pea ssRUBISCO E9 gene. [Fischhoff et al.]

Plant Transformation and Expression

A chimeric plant gene containing a structural coding sequence of the present invention can be inserted into the genome of a cotton plant by any suitable method. Suitable plant transformation vectors include those derived from a Ti plasmid of *Agrobacterium tumefaciens*, as well as those disclosed, e.g., by Herrera-Estrella (1983), Bevan (1983), Klee (1985) and EPO publication 0 120 516 (Schilperoort et al.). In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A particularly useful Ti plasmid cassette vector for transformation of dicotyledonous plants is pMON11782. The expression cassette pMON11782 consists of the FMV35S promoter, the petunia Hsp7O 5' untranslated leader, and the 3' end including polyadenylation signals from the pea ssRUBISCO E9 gene. Between the leader and the 3' polyadenylation signals is a multilinker containing multiple restriction sites, including a BamHI site for the insertion of genes. pMON 11782 also contains a HindIII site before the promoter sequence.

The remainder of pMON11782 contains a segment of pBR322 (New England Biolabs, Beverly, MA) which provides an origin of replication in *E. coli;* the oriV region from the broad host range plasmid RK1 which allows replication in *Agrobacterium* strain ABI; the streptomycin/spectinomycin resistance gene from Tn7; and a chimeric NPTII gene, containing the CaMV35S promoter and the nopaline synthase (NOS) 3' end, which provides kanamycin resistance in transformed plant cells.

Transient Expression of 3-Hydroxysteroid Oxidase in Tobacco Plants

Both 3-hydroxysteroid oxidase gene cassettes, that is the gene encoding intact protein with the signal sequence and that encoding only the mature protein, each modified at the N-terminus as described above, were mobilized as NcoI-BamHI fragments and inserted into a transient expression vector that had been cut with NcoI and BamHI. A transient expression vector is a simple plasmid containing a plant promoter with a 5' nontranslated leader, a 3' nontranslated polyadenylation sequence, and between them a multilinker having multiple restriction sites for insertion of a protein coding sequence. The constructed vectors placed the 3-hydroxysteroid oxidase gene under the control of the FMV35S promoter with the petunia HSP70 leader sequence discussed above. At the 3' end terminator region is the non-translated polyadenylation signal terminator region of the nopaline synthase gene. A plasmid containing the intact protein coding sequence (SEQ ID NO:13) was identified and named pMON 20910. A plasmid containing the modified mature protein coding sequence (SEQ ID NO:14) was identified and named pMON20908.

pMON20910 and pMON20908 are vectors for expression of 3-hydroxysteroid oxidase genes in plant cells, but these vectors lack appropriate sequences for use in Agrobacterium-mediated plant transformation. However, these vectors can be used for either transient expression of 3-hydroxysteroid oxidase in plant cells, or they can be used to generate stably transformed cotton plants via free DNA delivery such as biolistic bombardment of cotton meristems.

For transient expression analysis, plasmid DNA samples from pMON20908 and pMON20910 vectors were purified and introduced into tobacco via electroporation. Freeze-thaw extraction followed by a nine-fold concentration of soluble fractions on Centricon-10 filter concentrators allowed unambiguous detection of 3-hydroxysteroid oxidase activity in all cell lysates, immunologically by Western blot assay and enzymatically. The activity of the lysate from cells containing pMON20908, that is the coding sequence for the modified mature protein, was approximately ten-fold lower than that recovered from cells containing pMON20910. Western blot analysis indicated that the signal sequence is cleaved in protoplasts, although not necessarily with the fidelity necessary to generate a processed protein identical in form and activity to that naturally secreted by *Streptomyces* Al 9249.

Stable Transformation of Dicots with a 3-Hydroxysteroid Oxidase Gene pMON20910 containing the intact coding sequence was used to construct a vector for stable transformation of cotton plants with *Agrobacterium*. It was cut with restriction enzymes HindIII and BamHI. Such digestion creates HindIII-BamHI DNA fragments that contain the FMV35S promoter, the petunia Hsp70 leader, and the intact (full length) 3-hydroxysteroid oxidase coding sequence. These HindIII-BamHI fragments are inserted into plasmid pMON 11782, discussed above, which has been previously digested with HindIII-BamHI. pMON20912 was identified as containing the oxidase coding sequence. pMON20912 is thus composed of the FMV35S promoter, the petunia Hsp70 leader, the intact 3-hydroxysteroid oxidase coding sequence, and the 3' polyadenylation signal from the pea ssRUBISCO E9 gene.

This vector was introduced into disarmed *Agrobacterium* host ABI and used to transform cotton explants in tissue culture. Selection for kanamycin resistance led to several lines of cotton callus, which have been found to produce 3-hydroxysteroid oxidase as demonstrated by enzymatic activity and Western blot assay. After plant regeneration, whole cotton plants containing the 3-hydroxysteroid oxidase coding sequences will be recovered.

Vectors containing the intact or mature 3-hydroxysteroid oxidase cassette express the active enzyme in the cytoplasm of the plant cell. There has been no evidence of secretion outside the transformed cells. Some bacterial secretory signal sequences have been shown to function in plant cells. It may be desirable to direct most or all of the 3-hydroxysteroid oxidase protein into the plant secretory pathway. To achieve this, it may be advantageous to use a signal sequence derived from a plant gene rather than a bacterial signal. An example of such a signal is that from the tobacco PRIb gene, described by Comelissen et al. pMON10824, disclosed in EP Publ. 0385962, is a plant transformation vector designed for the expression of the lepidopteran active B.t. *kurstaki* protein. In pMON10824, the B.t.k. coding sequence is fused to the PRIb signal sequence plus 10 amino acids of the mature PRIb coding sequence. This B.t.k fusion gene is driven by the CaMV35S promoter containing a duplicated enhancer. To create a vector in which the PRIb signal is fused to the 3-hydroxysteroid oxidase gene, pMON10824 is first cut with BglII, and the large vector fragment is isolated. In a separate reaction, pMON10824 is cut with BglII and NcoI and the small BglII-NcoI fragment that contains the PRlb signal is isolated. In a ligation reaction, the BglII-cut pMON10824 is mixed with the small BglII-NcoI pMON10824 fragment plus the 3-hydroxy-steroid oxidase NcoI-BamHI cassette. This reaction constructs a plasmid in which the 3-hydroxysteroid oxidase coding sequence (either mature protein or intact protein cassette) is fused to the secretory signal from the PRlb gene and driven by the CaMV35S promoter. A similar plasmid may be constructed wherein the 3-hydroxysteroid oxidase gene is under the control of the FMV35S promoter. Such plasmids are mobilized into a disarmed *Agrobacterium* host and used to transform cotton plants. Thus, these plants produce a 3-hydroxy-steroid oxidase that is secreted into the extracellular space.

In some cases, proteins that enter the plant secretory pathway are targeted to different cellular compartments such as the vacuole. It may be desirable to direct the 3-hydroxysteroid oxidase to the vacuole of plant cells. In this case, the vectors described above in which the PRIb signal is used are further modified to include vacuolar targeting sequences derived from known plant vacuolar enzyme genes.

It may also be advantageous to direct the localization of the 3-hydroxysteroid oxidase protein to another cellular compartment, the chloroplast. Proteins can be directed to the chloroplast by including at their N-termini a chloroplast transit peptide (CTP). One CTP that has worked to localize heterologous proteins to the chloroplast is that derived from the RUBISCO small subunit gene of *Arabidopsis*, denoted ats1A. A variant of this transit peptide that encodes the transit pep-tide, 23 amino acids of mature RUBISCO sequence, plus a reiteration of the transit peptide cleavage site has been constructed for the successful chloroplast localization of the B.t.k. protein. Vectors containing the Arabidopsis ats1A transit peptide fused to the B.t.k. gene may be used as the base for constructing vectors for the chloroplast localization of the 3-hydroxysteroid oxidase protein. For example, pMON10821, constructed of an enhanced CaMV35S promoter, the ats1A chloroplast transit peptide and a truncated B.t.k. enzyme gene, disclosed in EP Publ. 0385962, is cut with BglII and the large BglII vector fragment is isolated. In a separate reaction, pMON10821 is cut with BglII and NcoI and the small BglII-NcoI fragment that contains the PRIb signal is isolated. In a ligation reaction, the BglII-cut pMON 10821 is mixed with the small BglII-NcoI pMON10821 fragment plus the 3-hydroxysteroid oxidase NcoI-BamHI cassette. This reaction constructs a plasmid in which the 3-hydroxy-steroid oxidase coding sequence (either mature protein or intact protein cassette) is fused to the Arabidopsis transit peptide with 23 amino acids of mature RUBISCO, and driven by the CaMV35S promoter. Alternatively, a similar plasmid may be constructed to replace the promoter with the FMV35S promoter. Such plasmids are mobilized into disarmed Agrobacterium hosts and used to transform cotton plants. Thus, these plants produce a 3-hydroxysteroid oxidase that is localized to the chloroplast.

Stable Transformation of Monocots

A 3-hydroxysteroid oxidase gene may be stably incorporated into the genome of monocots using the vectors and methods described in co-pending U.S. patent application Ser. No. 07/855,857, filed Mar. 19, 1992 (Brown et al.), which is hereby incorporated by reference. The gene can be inserted in an appropriate vector, for example pMON 19653 and 19643, described by Brown et al. The resulting construct contains a cassette of the CaMV E35S promoter, the Hsp70 intron, the CP4 glyphosate selection marker, and the NOS terminator; a cassette of the CaMV E35S promoter, the Hsp70 intron, the GOX glyphosate selection marker, and the NOS terminator; and a single NotI site for insertion of a gene expression cassette containing a 3-hydroxysteroid oxidase gene, such as SEQ ID NO:13 or SEQ ID NO:14.

This vector is inserted by bombardment of embryogenic tissue culture cells using a biolistic particle gun as described by Brown et al. Transformed cells are selected for glyphosate resistance and whole plants are regenerated. Insect-resistant plants may be confirmed to be expressing the gene by Western blot analysis, esterase activity assay, or insect resistance assay.

Targeting of the protein to certain cellular compartments is also possible in monocots using the signal sequences described above.

Evaluation of Synergistic Activity of B.t.[CryIA(c) or CryIA (b)] and Cholesterol Oxidase against Several Lepidopteran Pests Cholesterol oxidase is acutely toxic to boll weevil larvae ($LC_{50}$2 ppm in 16 day assay) but acute activity against lepidopteran larvae is generally limited to moderate stunting. The value of cholesterol oxidase as a synergist to B.t. was explored in diet assays with larvae of several lepidopterans. B.t. purified protein (either CryIA(c) or CryIA(b)) and cholesterol oxidase were tested alone and in tandem.

Tobacco budworm (TBW), and beet armyworm (BAW) were tested using CryIA(c) since these are cotton pests and the CryIA(c) protein has been expressed in cotton. European corn borer (ECB), black cutworm (BCW) and fall armyworm (FAW), being corn pests, were tested using CryIA(b). *Helicoverpa zea* (cotton bollworm, corn earworm) was tested using both CryIA proteins because of its pest status in both corn and cotton. Due to their extreme sensitivities to CryIA (c) and CryIA(b) respectively, TBW and ECB were challenged with low levels of these proteins so the additional effect of cholesterol oxidase would not be masked. In all other tests, the B.t. proteins were tested at concentrations (10–15 ppm) which were considered reasonable for expression levels in a transgenic plant. Likewise, and for the same reason, 15 ppm was chosen for the cholesterol oxidase test concentration. Feeding assays were conducted for 7–10 days. Results (both mortality and survivor-stunting) were evaluated for synergy using a model for independent joint action (Finney, 1964).

Figure 2:
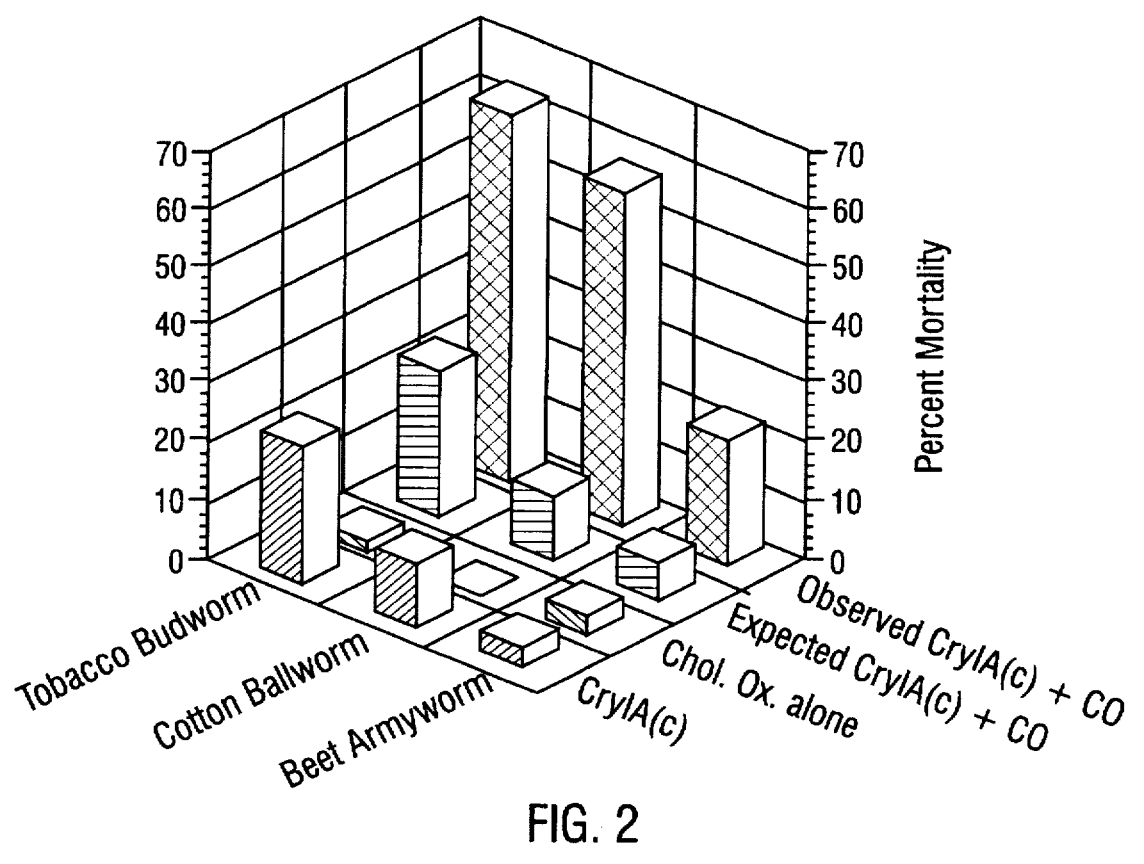
Figure 3:
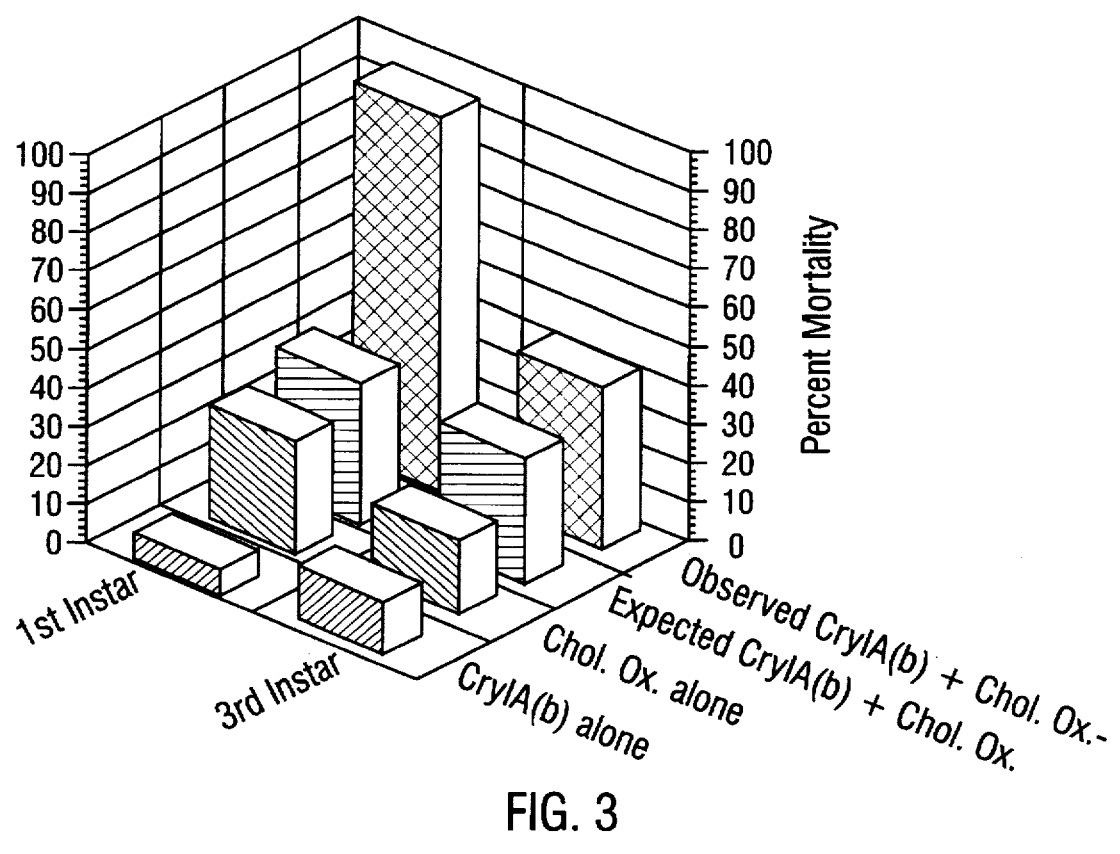

Results have been summarized graphically in FIG. 1, FIG. 2, FIG. 3 and Tables 14–23. When mentioned below, significance, in terms of synergistic responses, refers to statistical significance beyond what could be expected from additive, independent action.

TBW larvae were highly susceptible to CryIA(c)-cholesterol oxidase combinations in a manner that cannot be explained by simple additive effects. Highly significant synergy responses were observed when 15 ppm of cholesterol oxidase was added to 0.05 ppm of CryIA(c) (FIG. 2).

At 15 ppm of both CryIA(c) and cholesterol oxidase, BAW larvae responded with a mortality response that exceeded the expected value for additive effects, indicating significant synergistic activity (FIG. 2).

Statistically significant synergy was observed when CryIA(b) and cholesterol oxidase were combined at 15 ppm each against BCW neonate larvae. The mortality responses (FIG. 1) and, especially, the stunting response (FIG. 3) of BCW neonates to the combination treatment were significantly more severe than the responses expected if effects were simply additive. There was no such synergy apparent when the test organism was the more hardy 3rd instar BCW (FIG. 3).

No synergy was seen with CryIA(b) (10 ppm) and cholesterol oxidase at (15 ppm) when mortality responses of *H. zea* larvae were measured (FIG. 1). Significant synergy was apparent, however, in *H. zea* mortality responses to CryIA (c) and cholesterol oxidase (15 ppm for each) (FIG. 2).

ECB neonates, when challenged with 0.05 ppm CryIA(b) and 15 ppm cholesterol oxidase, exhibited a strong synergistic response (FIG. 1).

These results indicate the utility of cholesterol oxidase as a co-expressed protein to enhance the activity of B.t. against insects that are only moderately susceptible to B.t. (BAW, BCW). Cholesterol oxidase, expressed in cotton to control boll weevil, may also significantly enhance CryIA(c) activity against *Helicoverpa zea* and also function as a resistance management tool against the CryIA(c)-susceptible TBW. In a similar manner, cholesterol oxidase may also serve in a resistance management program for the CryIA(b)-sensitive ECB in corn.

TABLE 14

Responses of TBW neonate larvae to CryIA(c) protein and/or cholesterol oxidase either alone or in tandem (7-day feeding assay)

| Treatment | n | surv. | Obs. Mort. | Exp. Mort. | $X^2$ |
|---|---|---|---|---|---|
| Control | 96 | 91 | — | | |
| Chol. Ox. (CO) 15 ppm | 96 | 90 | 1% | | |
| CryIA(c) 0.1 ppm | 96 | 56 | 38% | | |
| CryIA(c) 0.1 ppm + | 96 | 16 | 82% | 39% | 47.4 (P << .005) |

TABLE 14-continued

Responses of TBW neonate larvae to CryIA(c) protein and/or cholesterol oxidase either alone or in tandem (7-day feeding assay)

| Treatment | n | surv. | Obs. Mort. | Exp. Mort. | $X^2$ |
|---|---|---|---|---|---|
| CO 15 ppm | | | | | |
| CryIA(c) 0.05 ppm | 96 | 70 | 23% | | |
| CryIA(c) 0.05 ppm + CO 15 ppm | 96 | 33 | 63% | 24% | 63.4 (P << .005) |

TABLE 15

Mortality responses of FAW neonate larvae to CryIA(b) protein and/or cholesterol oxidase either alone or in tandem (7-day feeding assay)

| Treatment | n | surv. | Obs. Mort. | Exp. Mort. | $X^2$ |
|---|---|---|---|---|---|
| Control | 87 | 87 | — | | |
| Chol. Ox. (CO) 15 ppm | 92 | 90 | 2% | | |
| CryIA(b) 15 ppm | 88 | 80 | 10% | | |
| CryIA(b) 15 ppm + CO 15 ppm | 87 | 79 | 7% | 12% | 2.1 NS |

TABLE 16

Stunting responses of FAW neonate larvae to CryIA(b) protein and/or cholesterol oxidase either alone or in tandem (7-day feeding assay)

| Treatment | Mean Larval wgt (mg) | Stunting Observed/Expected | | $X^2$ |
|---|---|---|---|---|
| Control | 43.03 ± 2.05 | | | |
| Chol. Ox(CO) 15 ppm | 42.97 ± 1.77 | 0% | | |
| CryIA(b) 15 ppm | 0.25 ± 0.05 | 99% | | |
| CryIA(b) 15 ppm + CO 15 ppm | 0.19 ± 0.04 | 99% | 99% | 0.0 NS |

TABLE 17

Mortality responses of BAW neonate larvae to CryIA(c) protein and/or cholesterol oxidase either alone or in tandem (7–8 day feeding assays).

| Treatment | n | surv. | Obs. Mort. | Exp. Mort. | $X^2$ |
|---|---|---|---|---|---|
| Control | | | | | |
| 7 day | 96 | 96 | — | | |
| 8 day | 72 | 72 | — | | |
| Chol. Ox. (CO) 15 ppm | | | | | |
| 7 day | 95 | 94 | 1% | | |
| 8 day | 79 | 77 | 3% | | |
| CryIA(c) 15 ppm | | | | | |
| 7 day | 96 | 94 | 2% | | |
| 8 day | 72 | 70 | 3% | | |
| CryIA(c) 15 ppm + CO 15 ppm | | | | | |
| 7 day | 90 | 82 | 9% | 3% | 12.0 (P < 0.005) |
| 8 day | 58 | 46 | 21% | 6% | 27.5 (P << 0.005) |

TABLE 18

Stunting responses of BAW neonate larvae to CryIA(c) protein and/or cholesterol oxidase either alone or in tandem (7-day feeding assay)

| Treatment | Mean Larval wgt (mg) | Stunting Observed/Expected | | $X^2$ |
|---|---|---|---|---|
| Control | 52.12 ± 4.81 | | | |
| Chol. Ox (CO) 15 ppm | 27.51 ± 5.52 | 47% | | |
| CryIA(c) 15 ppm | 6.15 ± 0.90 | 88% | | |
| CryIA(c) 15 ppm + CO 15 ppm | 0.41 ± 0.10 | 99% | 94% | 0.3 NS |

TABLE 19

Mortality responses of BCW larvae to CryIA(b) protein and/or cholesterol oxidase either alone or in tandem (6–7 day feeding assays)

| Treatment | n | surv. | Obs. Mort. | Exp. Mort. | $X^2$ |
|---|---|---|---|---|---|
| Control | | | | | |
| Neonate 6 day | 94 | 90 | — | | |
| Neonate 7 day | 78 | 76 | — | | |
| 3rd instar 6 day | 31 | 31 | — | | |
| Chol: Ox. (CO) 15 ppm | | | | | |
| Neonate 6 day | 86 | 81 | 2% | | |
| Neonate 7 day | 63 | 61 | 1% | | |
| 3rd instar 6 day | 32 | 32 | 0% | | |
| CryIA(b) 15 ppm | | | | | |
| Neonate 6 day | 95 | 91 | 0% | | |
| Neonate 7 day | 80 | 76 | 2% | | |
| 3rd instar 6 day | 32 | 32 | 0% | | |
| CryIA(b) 15 ppm + CO 15 ppm | | | | | |
| Neonate 6 day | 96 | 81 | 12% | 2% | 50.0 (P << 0.005) |
| Neonate 7 day | 72 | 50 | 29% | 3% | 225 (P << 0.005) |
| 3rd instar 6 day | 32 | 32 | 0% | 0% | 0 NS |

TABLE 20

Stunting responses of BCW larvae to CryIA(b) protein and/or cholesterol oxidase either alone or in tandem (7-day assay for neonates; 6-day assay for 3rd instars)

| Treatment | Mean Larval wgt (mg) | Stunting Observed/ | Expected | $X^2$ |
|---|---|---|---|---|
| Control | | | | |
| Neonate | 14.60 ± 0.89 | | | |
| 3rd instar | 253 ± 8 | | | |
| Chol. Ox. (CO) 15 ppm | | | | |
| Neonate | 9.93 ± 1.32 | 32% | | |
| 3rd instar | 197 ± 11 | 22% | | |
| CryIA(b) 15 ppm | | | | |
| Neonate | 13.64 ± 1.17 | 7% | | |
| 3rd instar | 216 ± 8 | 15% | | |
| CryIA(b) 15 ppm + CO 15 ppm | | | | |
| Neonate | 0.89 ± 0.30 | 94% | 37% | 87.8 (P << 0.005) |
| 3rd instar | 150 ± 11 | 41% | 34% | 1.2 NS |

TABLE 21

Mortality responses of *H. zea* neonate larvae to CryIA(b) protein and/or cholesterol oxidase either alone or in tandem (7–8 day feeding assays)

| Treatment | n | surv. | Obs. Mort. | Exp. Mort. | $X^2$ |
|---|---|---|---|---|---|
| Control | | | | | |
| 7 day | 96 | 94 | — | | |
| 8 day | 85 | 85 | — | | |
| Chol. Ox. (CO) 15 ppm | | | | | |
| 7 day | 96 | 95 | 0% | | |
| 8 day | 88 | 87 | 1% | | |
| CryIA(b) 10 ppm | | | | | |
| 7day | 96 | 90 | 4.3% | | |
| 8day | 77 | 69 | 10% | | |
| CryIA(b) 10 ppm + CO 15 ppm | | | | | |
| 7 day | 95 | 86 | 7.6% | 4.3% | 2.5 NS |
| 8 day | 76 | 65 | 14% | 11% | 0.6 NS |

TABLE 22

Stunting responses of *H. zea* neonate larvae to CryIA(b) protein and/or cholesterol oxidase either alone or in tandem (7-day feeding assay)

| Treatment | Mean Larval wgt (mg) | Stunting Observed/ | Expected | $X^2$ |
|---|---|---|---|---|
| Control | 34.28 ± 3.55 | | | |
| Chol. Ox. (CO) 15 ppm | 24.95 ± 4.79 | 27% | | |
| CryIA(b) 10 ppm | 0.96 ± 0.39 | 97% | | |
| CryIA(b) 10 ppm + CO 15 ppm | 0.45 ± 0.12 | 99% | 98% | 0.01 NS |

TABLE 23

Mortality responses of H. zea neonate larvae to CryIA(c) protein and/or cholesterol oxidase either alone or in tandem (7 & 10-day feeding assays)

| Treatment | n | surv. | Obs. Mort. | Exp. Mort. | $X^2$ |
|---|---|---|---|---|---|
| Control | | | | | |
| 7 day | 96 | 96 | — | | |
| 10 day | 96 | 96 | — | | |
| Chol. Ox (CO) 15 ppm | | | | | |
| 7 day | 96 | 96 | 0% | | |
| 10 day | 96 | 96 | 0% | | |
| CryIA(c) 15 ppm | | | | | |
| 7 day | 92 | 82 | 11% | | |
| 10 day | 92 | 82 | 11% | | |
| CryIA(c) 15 ppm + CO 15 ppm | | | | | |
| 7 day | 95 | 72 | 24% | 11% | 15.4 (P < 0.005) |
| 10 day | 95 | 42 | 56% | 11% | 184 (P < 0.005) |

In Planta evaluation of biological activity of CryIA(b) in tandem with cholesterol oxidase and CryIA(b) alone against BCW.

A detached leaf assay was designed to evaluate biological activity of transgenic corn expressing either CryIA(b) alone or in combination with cholesterol oxidase (CO) against Agrotis ipsilon, black cutworm (BCW). In artificial diet assays, a synergistic response was observed when CO and CryIA(b) were combined.

Assay Design

Treatments included transgenic corn expressing either CryIA(b) alone or in combination with CO. Plant tissue from the F1 generation of two CO events crossed to a CryIA(b) event was used in this bioassay. The CO events included collosian and flushed. The CryIA(b) event was ezra. For each of the CO events by CryIA(b) cross, the CO isopopulations provide the tissue for each treatment.

CO expression was estimated to be 15 and 14 ppm for collosian and flushed, respectively. CryIA(b) expression was not quantitated. Historically, this event has reliably and consistently expressed the CryIA(b) protein at around 10 ppm.

Tissue was collected at the v6 stage from the youngest leaf of six plants for each treatment event combination. Four leaf samples (1.5×2.0 cm leaf pieces) were taken from each plant, where each piece was placed singly in a well of a 24-well microtiter plate. One neonate larva was added to each well and sealed with a mylar lidding. The assay was incubated for 3 days at 27° C. Larval weight (mg) and mortality was recorded. Mean weights and mortality were calculated for each CO event by treatment combination Table 24 shows the mortality and larval weight responses. Although larval weight was less in the CryIA(b)+CO treatment for both events as compared to CryIA(b) alone (ca. 12%), the difference between the treatment means within an event was not significant. Mortality also did not differ significantly between treatments.

BCW larvae were highly susceptible to CryIA(b)+CO combinations in an artificial diet assay in a manner that cannot be explained by simple additive effects when exposed to the individual proteins. However, when these proteins were expressed together in planta at similar levels used in the diet assay, there were no observed differences in larval weight or mortality between CryIA(b)+CO and CryIA(b) treatments.

TABLE 24

Mortality and stunting response of BCW neonate to corn plants expressing CryIA(b) alone or in tandem with cholesterol oxidase in a 3d detached leaf assay

| Event | Treatment | $N^a$ | Mean Larval Weight (mg) | SE | $Mort^b$ (%) |
|---|---|---|---|---|---|
| collosian | CryIA(b) | 24 | 1.11 | 0.10 | 7 |
| | CryIA(b) + CO | 24 | 0.99 | 0.09 | 5 |
| flushed | CryIA(b) | 24 | 1.27 | 0.06 | 8 |
| | CryIA(b) + CO | 24 | 1.12 | 0.09 | 6 |

[a] number of observations.
[b] Mort. = Mortality.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

REFERENCES

The following literature citations as well as those cited above are incorporated in pertinent part by reference herein for the reasons cited in the above text.

Bagdasarian M., Lurz R., Ruckert B., Franklin F., Bagdasarian M. M., and Timmis K. N, "Specific purpose cloning vectors. II. Broad host range, high copy number RSF1010-derived vectors and a host vector system for gene cloning in Pseudomonas," Gene, 16:237–47, 1981.

Bevan M et al., Nature, 304:184, 1983.

Burnnette W. N., "Western blotting: Electrophoretic transfer of proteins from SDS-PAGE gels to unmodified nitrocellulose and radiographic detection with antibody and radioiodinated proteins," Anal. Biochem., 112:195–203, 1981.

Cornelissen B. J. C. et al., EMBO Journal, 5:37–40, 1986.

Finney, D. J. "Probit Analysis", Cambridge University Press, London, 1964.

Fischhoff D. A. and Perlak F. J., "Synthetic plant genes and method for preparation." European Patent Application, Publication Number 0 385 962, 1990.

Gallo L. L., "Pancreatic sterol esterhydrolase," Methods Enzymol., 71:665–7, 1981.

Herrera-Estrella L. et al., Nature, 303:209, 1983.

Ishizaki T., Hirayam N., Shinkawa H., Nimi O., Murooka Y, "Nucleotide Sequence of the Gene for Cholesterol Oxidase from a Streptomyces sp," Journal of Bacteriology, 171:596–601, 1989.

Kay R. et al., Science, 236:1299–1302, 1987.

Klee H. J. et al., Bio/Technology, 3:637–642, 1985.

Knauf V. C. and Nester E, "Wide host range cloning vectors: A cosmid bank of an Agrobacterium Ti plasmid." Plasmid, 8:43–54, 1982.

Laemmli U.K., "Cleavage of structural proteins during the assembly of the head of bacteriophage T4," *Nature*, 227:680–5, 1970.

Long Susan and Ostroff Gary R., "Cloning and expression of cholesterol oxidase gene of Nocardioform bacteria," PCT Int. Appl. WO 9005,788.

Marrone P. G., Ferri F. D., Mosley T. R., Meinke L. J., "Improvements in laboratory rearing of the southern corn rootworm, *Diabrotica undecimpunctata howardi* Barber (Coleoptera: Chrysomelidae) on artificial diet and corn," *Journal of Economic Entomology*, 78:290–3, 1985.

Matsudaira P., "Sequence from picomole quantities of proteins electroblotted onto polyvinylidene difluoride membranes," *Journal of Biol. Chem.*, 261:10035–38, 1987.

Moore S. and Stein W. H., "Chromatographic determination of amino acids by the use of automatic recording equipment," *Methods in Enzymology*, 6:819–31, 1963.

Purcell J. P., Greenplate J. T., and Sarrimons R. P., "Examination of midgut luminal proteinase activities in six economically important insects," *Insect Biochem. Molec. Biol.*, 22:41–47, 1992.

Schuler M. A. et al, *NucleicAcids Research*, 10:8225–8244, 1982.

Smith A. G. and Brooks C. J. W., "Cholesterol oxidases: Properties and Applications," *Journal of Steroid Biochemistry*, 7:705–713, 1976.

Smith P. K., Krohn R. L., Hermanson G. T., Mallia A. K., Gartner F. H., Provenzano M. D., Fujimoto E. K., Goeke M. N., Olson B. J., Klenk D. C., "Measurement of protein using bicinchoninic acid," *Analytical Biochemistry*, 150:76–85, 1985.

Winter et al Mol Gen. Genet., 221(2):315–19, 1988.

Yanisch-Perron C., Viera J., and Messing J., "Improved M13 phage cloning vectors and host strains: nucleotide sequences of the M13mp18 and pUC19 vectors," *Gene*, 33:103–19, 1985.

What is claimed is:

1. A method of controlling insect infestation of plants comprising providing a 3-hydroxysteroid oxidase and a CrylA *Bacillus thuringiensis* protein in an insecticidally effective amount for ingestion by the insect where the insect is identified as a lepidopteran.

2. The method of claim 1 wherein the insect is in a larval stage.

3. The method of claim 1 wherein the CryIA is CryIA(c).

4. The method of claim 1 wherein the CryIA is CryIA(b).

5. The method of claim 3 wherein the insect is tobacco budworm or beet armyworm.

6. The method of claim 4 wherein the insect is European corn borer, black cutworm or fall armyworm.

7. The method of claim 4 wherein the insect is cotton bollworm or corn earworm.

8. The method of claim 1 wherein the insecticidally effective amount is between about 8 and about 20 ppm.

9. A recombinant expression vector comprising nucleic acid sequences encoding a CrylA protein and a 3-hydroxysteroid oxidase, each sequence operatively linked to a promoter to express separately or in tandem said nucleic acid sequences to produce said CrylA protein and said 3-hydroxysteroid in a plant cell.

10. The vector of claim 9 wherein the plant cell is identified as a corn cell.

11. A method of producing a genetically transformed plant which produces an insecticidally effective amount of a CrylA protein and a 3-hydroxysteroid oxidase, comprising inserting into the genome of a plant cell a recombinant vector comprising:

a) a sequence encoding 3-hydroxysteroid oxidase;

b) a sequence encoding a CrylA protein; and, c) at least one promoter that functions in a plant cell which promoter is heterologous with respect to said coding sequences operatively linked to effect expression of said coding sequences to produce the CrylA protein and the 3-hydroxysteroid oxidase in an insecticidally effective amount in a genetically transformed plant obtained from the plant cell.

12. The method of claim 11 wherein the plant is a cotton plant.

13. The method of claim 11 wherein the plant is a corn plant.

14. A plant produced by the method of claim 11.

15. A seed produced by the plant of claim 11.

16. The seed of claim 15 which is a cotton seed or a corn seed.

17. The method of claim 11 wherein the CrylA protein is identified as a CryIA(b) protein.

18. The method of claim 11 wherein the CrylA protein is identified as a CryIA(c) protein.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Val  Ser  Thr  Leu  Met  Leu  Glu  Met  Gly  Gln  Leu  Trp  Asn  Gln  Pro
 1              5                        10                           15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ala  Phe  Ala  Asp  Asp  Phe  Cys  Tyr  His  Pro  Leu  Gly  Gly  Cys  Val  Leu
 1              5                         10                            15
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Asn  Leu  Tyr  Val  Thr  Asp  Gly  Ser  Leu  Ile  Pro  Gly
 1              5                        10
```

( 2 ) INFORMATION FOR SEQ ID NO:4:

( i ) SEQUENCE CHARACTERISTICS:
   ( A ) LENGTH: 45 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:4:

| GTGTCCACCC TGATGCTGGA GATGGGCCAG CTGTGGAACC AGCCC | 45 |

( 2 ) INFORMATION FOR SEQ ID NO:5:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

| GCCTTCGCCG ACGACTTCTG CTACCACCCG CTCGGCGGCT GCGTCCTG | 48 |

( 2 ) INFORMATION FOR SEQ ID NO:6:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

| AACCTCTACG TGACCGACGG TTCGCTGATC CCGGGT | 36 |

( 2 ) INFORMATION FOR SEQ ID NO:7:

( i ) SEQUENCE CHARACTERISTICS:
      ( A ) LENGTH: 1865 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

| CTACTCCATG GCGTGCTGAA GGTCGGTGCC TGGCCTCCCG AGGTCGTCGA GGACTTCGTG | 60 |
| AAGTGAGCGG GCACCCCGCC CGTCCCCGCC CCGCAACGGC CCGTTCCGCA CACCGGGTGA | 120 |
| CCCGACCCCC TCGGCCCCCG ACGTCCGCCG ACCTCTCAGT CCCCTCTCGA AGCTCAGGAG | 180 |
| CAACAGCGTG AACGCACACC AGCCTCTGTC GCGCCGCCGC ATGCTCGGCC TGGCCGCCTT | 240 |
| GGGCGCCGCC GCACTCACCG GCAGACCAC GATCACCGCG GCCCCCGCG CGGCCGCCGC | 300 |
| CACCGCCCCC GGCGGCTCCG GCGGCACGTT CGTGCCCGCC GTCGTGATCG GCACCGGCTA | 360 |
| CGGCGCGGCC GTCTCCGCCC TGCGGCTCGG CGAGGCCGGG GTCTCCACCC TGATGCTGGA | 420 |
| GATGGGCCAG CTGTGGAACC AGCCCGGCCC GGACGGCAAC GTCTTCTGCG GATGCTCAA | 480 |
| GCCCGACAAG CGCTCCAGCT GGTTCAAGAC CCGCACCGAG GCCCGCTCG GCTCCTTCCT | 540 |
| CTGGCTCGAC CTCGCCAACC GGGACATCGA CCCCTACGCG GGCGTCCTGG ACCGGGTCAA | 600 |
| CTTCGACCAG ATGTCCGTGT ACGTGGGCCG CGGGGTCGGC GGCGGCTCGC TCGTCAACGG | 660 |
| CGGTATGGCC GTCACGCCCC GGCGCTCCTA CTTCCAGGAG GTGCTGCCCC AGGTCGACGC | 720 |

```
CGACGAGATG  TACGGCACCT  ACTTCCCGCG  CGCGAACTCC  GGCCTGCGGG  TCAACAACAT    780
CGACAAGGAC  TGGTTCGAGC  AGACCGAGTG  GTACACGTTC  GCGCGCGTTG  CCCGTCTGCA    840
GGCCGAGAAC  GCCGGCCTGA  AGACCACCTT  CGTGCCCAAC  GTCTACGACT  GGGACTACAT    900
GCGCGGTGAG  GCGGACGGCA  CCAACCCCAA  GTCCGCGCTC  GCCGCCGAGG  TCATCTACGG    960
CAACAACCAC  GGCAAGGTCT  CCCTCGACAA  GAGCTACCTG  GCGGCCGCCC  TGGGCACCGG   1020
CAAGGTCACC  GTCGAGACCC  TGCACCAGGT  CAAGACGATC  CGTCAGCAGA  ACGACGGCAC   1080
CTACCTGCTG  ACGGTCGAGC  AGAAGGACCC  CGACGGCAAG  CTGCTCGGGA  CCAAGGAGAT   1140
CTCCTGCCGC  CACCTCTTCC  TCGGCGCCGG  CAGCCTCGGC  TCCATTGAAC  TGCTGCTGCG   1200
CGCCCGGGAG  ACCGGCACCC  TGCCCGGCCT  CAGCTCCGAG  ATCGGCGGCG  GCTGGGCCC   1260
CAACGGCAAC  ATCATGACCG  CCCGCGCCAA  CCATGTGTGG  AACCCCACGG  GCAGCAAGCA   1320
GTCGTCGATC  CCCGCCCTCG  GCATCGACGA  CTGGGACAAC  CCCGACAACC  CCGTCTTCGC   1380
CGAGATAGCC  CCCATGCCGG  CGGGCCTCGA  GACCTGGGTC  AGCCTCTACC  TGGCCATCAC   1440
CAAGAACCCG  GAGCGCGGCA  CCTTCGTCTA  CGACGCCGCC  AAGGACCGGG  CGGACCTGCG   1500
CTGGACCCGG  GACCAGAACG  CGCCCGCGGT  CGCCGCCGCC  AAGTCGCTGT  CGACCGCGT   1560
CAACAAGGCC  AACACGACCA  TCTACCGGTA  CGACCTCTTC  GGCAAGCAGA  TCAAGGCGTT   1620
CGCCGACGAC  TTCTGCTACC  ACCCGCTCGG  CGGCTGCGTC  CTCGGCAAGG  CCACCGACAA   1680
CTACGGCCGC  GTCTCCGGGT  ACAAGAACCT  CTACGTCACC  GACGGCTCGC  TCATCCCCGG   1740
CAGCATCGGC  GTCAACCCGT  TCGTGACCAT  CACGGCGCTG  GCGGAGCGGA  ACGTCGAGCG   1800
CGTCATCAAG  GAGGACATCG  CGGGTTCCTG  ACGAGCGACG  GGCGGGGCGC  GGCATGCAAG   1860
CTTGG                                                                    1865
```

( 2 ) INFORMATION FOR SEQ ID NO:8:

( i ) SEQUENCE CHARACTERISTICS:
        ( A ) LENGTH: 547 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Val  Asn  Ala  His  Gln  Pro  Leu  Ser  Arg  Arg  Arg  Met  Leu  Gly  Leu  Ala
  1              5                        10                        15

Ala  Leu  Gly  Ala  Ala  Ala  Leu  Thr  Gly  Gln  Thr  Thr  Ile  Thr  Ala  Ala
                20                       25                        30

Pro  Arg  Ala  Ala  Ala  Ala  Thr  Ala  Pro  Gly  Gly  Ser  Gly  Gly  Thr  Phe
          35                       40                        45

Val  Pro  Ala  Val  Val  Ile  Gly  Thr  Gly  Tyr  Gly  Ala  Ala  Val  Ser  Ala
     50                       55                        60

Leu  Arg  Leu  Gly  Glu  Ala  Gly  Val  Ser  Thr  Leu  Met  Leu  Glu  Met  Gly
 65                       70                        75                        80

Gln  Leu  Trp  Asn  Gln  Pro  Gly  Pro  Asp  Gly  Asn  Val  Phe  Cys  Gly  Met
                    85                        90                        95

Leu  Lys  Pro  Asp  Lys  Arg  Ser  Ser  Trp  Phe  Lys  Thr  Arg  Thr  Glu  Ala
               100                       105                       110

Pro  Leu  Gly  Ser  Phe  Leu  Trp  Leu  Asp  Leu  Ala  Asn  Arg  Asp  Ile  Asp
          115                       120                       125

Pro  Tyr  Ala  Gly  Val  Leu  Asp  Arg  Val  Asn  Phe  Asp  Gln  Met  Ser  Val
     130                       135                       140

Tyr  Val  Gly  Arg  Gly  Val  Gly  Gly  Ser  Leu  Val  Asn  Gly  Gly  Met
```

```
145                 150                  155                 160
Ala Val Thr Pro Arg Ser Tyr Phe Gln Glu Val Leu Pro Gln Val
                165             170             175
Asp Ala Asp Glu Met Tyr Gly Thr Tyr Phe Pro Arg Ala Asn Ser Gly
            180             185             190
Leu Arg Val Asn Asn Ile Asp Lys Asp Trp Phe Glu Gln Thr Glu Trp
        195             200             205
Tyr Thr Phe Ala Arg Val Ala Arg Leu Gln Ala Glu Asn Ala Gly Leu
    210             215             220
Lys Thr Thr Phe Val Pro Asn Val Tyr Asp Trp Asp Tyr Met Arg Gly
225             230             235                     240
Glu Ala Asp Gly Thr Asn Pro Lys Ser Ala Leu Ala Ala Glu Val Ile
            245             250             255
Tyr Gly Asn Asn His Gly Lys Val Ser Leu Asp Lys Ser Tyr Leu Ala
            260             265             270
Ala Ala Leu Gly Thr Gly Lys Val Thr Val Glu Thr Leu His Gln Val
        275             280             285
Lys Thr Ile Arg Gln Gln Asn Asp Gly Thr Tyr Leu Leu Thr Val Glu
    290             295             300
Gln Lys Asp Pro Asp Gly Lys Leu Leu Gly Thr Lys Glu Ile Ser Cys
305             310             315                     320
Arg His Leu Phe Leu Gly Ala Gly Ser Leu Gly Ser Ile Glu Leu Leu
            325             330             335
Leu Arg Ala Arg Glu Thr Gly Thr Leu Pro Gly Leu Ser Ser Glu Ile
            340             345             350
Gly Gly Gly Trp Gly Pro Asn Gly Asn Ile Met Thr Ala Arg Ala Asn
        355             360             365
His Val Trp Asn Pro Thr Gly Ser Lys Gln Ser Ser Ile Pro Ala Leu
    370             375             380
Gly Ile Asp Asp Trp Asp Asn Pro Asp Asn Pro Val Phe Ala Glu Ile
385             390             395                     400
Ala Pro Met Pro Ala Gly Leu Glu Thr Trp Val Ser Leu Tyr Leu Ala
            405             410             415
Ile Thr Lys Asn Pro Glu Arg Gly Thr Phe Val Tyr Asp Ala Ala Lys
            420             425             430
Asp Arg Ala Asp Leu Arg Trp Thr Arg Asp Gln Asn Ala Pro Ala Val
        435             440             445
Ala Ala Ala Lys Ser Leu Phe Asp Arg Val Asn Lys Ala Asn Thr Thr
    450             455             460
Ile Tyr Arg Tyr Asp Leu Phe Gly Lys Gln Ile Lys Ala Phe Ala Asp
465             470             475                     480
Asp Phe Cys Tyr His Pro Leu Gly Gly Cys Val Leu Gly Lys Ala Thr
            485             490             495
Asp Asn Tyr Gly Arg Val Ser Gly Tyr Lys Asn Leu Tyr Val Thr Asp
            500             505             510
Gly Ser Leu Ile Pro Gly Ser Ile Gly Val Asn Pro Phe Val Thr Ile
        515             520             525
Thr Ala Leu Ala Glu Arg Asn Val Glu Arg Val Ile Lys Glu Asp Ile
    530             535             540
Ala Gly Ser
545
```

( 2 ) INFORMATION FOR SEQ ID NO:9:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:9:

CTCAGGAGCA CCATGGCGAC CGCACAC 27

( 2 ) INFORMATION FOR SEQ ID NO:10:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:10:

GTGCCGCCGG AGGCCATGGG GGCGGTGGC 29

( 2 ) INFORMATION FOR SEQ ID NO:11:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

GCCCCGCCCG TCGGATCCGT CAGGAACCCG 30

( 2 ) INFORMATION FOR SEQ ID NO:12:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

Ser Gly Gly Thr Phe
1               5

( 2 ) INFORMATION FOR SEQ ID NO:13:

( i ) SEQUENCE CHARACTERISTICS:
  ( A ) LENGTH: 1647 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| ATGGCGACCG | CACACCAGCC | TCTGTCGCGC | CGCCGCATGC | TCGGCCTGGC | CGCCTTGGGC | 60 |
| GCCGCCGCAC | TCACCGGGCA | GACCACGATC | ACCGCGGCCC | CCGCGCGGC | CGCCGCCACC | 120 |
| GCCCCGGCG | GCTCCGGCGG | CACGTTCGTG | CCCGCCGTCG | TGATCGGCAC | CGGCTACGGC | 180 |
| GCGGCCGTCT | CCGCCCTGCG | GCTCGGCGAG | GCCGGGGTCT | CCACCCTGAT | GCTGGAGATG | 240 |
| GGCCAGCTGT | GGAACCAGCC | CGGCCCGGAC | GGCAACGTCT | TCTGCGGGAT | GCTCAAGCCC | 300 |

```
GACAAGCGCT CCAGCTGGTT CAAGACCCGC ACCGAGGCCC CGCTCGGCTC CTTCCTCTGG    360
CTCGACCTCG CCAACCGGGA CATCGACCCC TACGCGGGCG TCCTGGACCG GGTCAACTTC    420
GACCAGATGT CCGTGTACGT GGGCCGCGGG GTCGGCGGCG GCTCGCTCGT CAACGGCGGT    480
ATGGCCGTCA CGCCCCGGCG CTCCTACTTC CAGGAGGTGC TGCCCCAGGT CGACGCCGAC    540
GAGATGTACG GCACCTACTT CCCGCGCGCG AACTCCGGCC TGCGGGTCAA CAACATCGAC    600
AAGGACTGGT TCGAGCAGAC CGAGTGGTAC ACGTTCGCGC GCGTTGCCCG TCTGCAGGCC    660
GAGAACGCCG GCCTGAAGAC CACCTTCGTG CCCAACGTCT ACGACTGGGA CTACATGCGC    720
GGTGAGGCGG ACGGCACCAA CCCCAAGTCC GCGCTCGCCG CCGAGGTCAT CTACGGCAAC    780
AACCACGGCA AGGTCTCCCT CGACAAGAGC TACCTGGCGG CCGCCCTGGG CACCGGCAAG    840
GTCACCGTCG AGACCCTGCA CCAGGTCAAG ACGATCCGTC AGCAGAACGA CGGCACCTAC    900
CTGCTGACGG TCGAGCAGAA GGACCCCGAC GGCAAGCTGC TCGGGACCAA GGAGATCTCC    960
TGCCGCCACC TCTTCCTCGG CGCCGGCAGC CTCGGCTCCA TTGAACTGCT GCTGCGCGCC   1020
CGGGAGACCG GCACCCTGCC CGGCCTCAGC TCCGAGATCG GCGGCGGCTG GGGCCCCAAC   1080
GGCAACATCA TGACCGCCCG CGCCAACCAT GTGTGGAACC CCACGGGCAG CAAGCAGTCG   1140
TCGATCCCCG CCCTCGGCAT CGACGACTGG GACAACCCCG ACAACCCCGT CTTCGCCGAG   1200
ATAGCCCCCA TGCCGGCGGG CCTCGAGACC TGGGTCAGCC TCTACCTGGC CATCACCAAG   1260
AACCCGGAGC GCGGCACCTT CGTCTACGAC GCCGCCAAGG ACCGGGCGGA CCTGCGCTGG   1320
ACCCGGGACC AGAACGCGCC CGCGGTCGCC GCCGCCAAGT CGCTGTTCGA CCGCGTCAAC   1380
AAGGCCAACA CGACCATCTA CCGGTACGAC CTCTTCGGCA AGCAGATCAA GGCGTTCGCC   1440
GACGACTTCT GCTACCACCC GCTCGGCGGC TGCGTCCTCG GCAAGGCCAC CGACAACTAC   1500
GGCCGCGTCT CCGGGTACAA GAACCTCTAC GTCACCGACG GCTCGCTCAT CCCCGGCAGC   1560
ATCGGCGTCA ACCCGTTCGT GACCATCACG GCGCTGGCGG AGCGGAACGT CGAGCGCGTC   1620
ATCAAGGAGG ACATCGCGGG TTCCTGA                                       1647
```

( 2 ) INFORMATION FOR SEQ ID NO:14:

( i ) SEQUENCE CHARACTERISTICS:
        ( A ) LENGTH: 1521 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
ATGGCCTCCG GCGGCACGTT CGTGCCCGCC GTCGTGATCG GCACCGGCTA CGGCGCGGCC     60
GTCTCCGCCC TGCGGCTCGG CGAGGCCGGG GTCTCCACCC TGATGCTGGA GATGGGCCAG    120
CTGTGGAACC AGCCCGGCCC GGACGGCAAC GTCTTCTGCG GGATGCTCAA GCCCGACAAG    180
CGCTCCAGCT GGTTCAAGAC CCGCACCGAG GCCCGCTCG GCTCCTTCCT CTGGCTCGAC    240
CTCGCCAACC GGGACATCGA CCCCTACGCG GGCGTCCTGG ACCGGGTCAA CTTCGACCAG    300
ATGTCCGTGT ACGTGGGCCG CGGGGTCGGC GGCGGCTCGC TCGTCAACGG CGGTATGGCC    360
GTCACGCCCC GGCGCTCCTA CTTCCAGGAG GTGCTGCCCC AGGTCGACGC CGACGAGATG    420
TACGGCACCT ACTTCCCGCG CGCGAACTCC GGCCTGCGGG TCAACAACAT CGACAAGGAC    480
TGGTTCGAGC AGACCGAGTG GTACACGTTC GCGCGCGTTG CCCGTCTGCA GGCCGAGAAC    540
GCCGGCCTGA AGACCACCTT CGTGCCCAAC GTCTACGACT GGGACTACAT GCGCGGTGAG    600
GCGGACGGCA CCAACCCCAA GTCCGCGCTC GCCGCCGAGG TCATCTACGG CAACAACCAC    660
```

-continued

```
GGCAAGGTCT CCCTCGACAA GAGCTACCTG GCGGCCGCCC TGGGCACCGG CAAGGTCACC   720

GTCGAGACCC TGCACCAGGT CAAGACGATC CGTCAGCAGA ACGACGGCAC CTACCTGCTG   780

ACGGTCGAGC AGAAGGACCC CGACGGCAAG CTGCTCGGGA CCAAGGAGAT CTCCTGCCGC   840

CACCTCTTCC TCGGCGCCGG CAGCCTCGGC TCCATTGAAC TGCTGCTGCG CGCCCGGGAG   900

ACCGGCACCC TGCCCGGCCT CAGCTCCGAG ATCGGCGGCG GCTGGGGCCC CAACGGCAAC   960

ATCATGACCG CCCGCGCCAA CCATGTGTGG AACCCCACGG GCAGCAAGCA GTCGTCGATC  1020

CCCGCCCTCG GCATCGACGA CTGGGACAAC CCCGACAACC CCGTCTTCGC CGAGATAGCC  1080

CCCATGCCGG CGGGCCTCGA GACCTGGGTC AGCCTCTACC TGGCCATCAC CAAGAACCCG  1140

GAGCGCGGCA CCTTCGTCTA CGACGCCGCC AAGGACCGGG CGGACCTGCG CTGGACCCGG  1200

GACCAGAACG CGCCCGCGGT CGCCGCCGCC AAGTCGCTGT TCGACCGCGT CAACAAGGCC  1260

AACACGACCA TCTACCGGTA CGACCTCTTC GGCAAGCAGA TCAAGGCGTT CGCCGACGAC  1320

TTCTGCTACC ACCCGCTCGG CGGCTGCGTC CTCGGCAAGG CCACCGACAA CTACGGCCGC  1380

GTCTCCGGGT ACAAGAACCT CTACGTCACC GACGGCTCGC TCATCCCCGG CAGCATCGGC  1440

GTCAACCCGT TCGTGACCAT CACGGCGCTG GCGGAGCGGA ACGTCGAGCG CGTCATCAAG  1500

GAGGACATCG CGGGTTCCTG A                                            1521
```